(12) United States Patent
Skach et al.

(10) Patent No.: US 9,188,592 B2
(45) Date of Patent: Nov. 17, 2015

(54) FLUORESCENT DETECTION OF IN VITRO TRANSLATED PROTEIN ON A SOLID SURFACE

(71) Applicants: William Skach, Portland, OR (US); LeeAnn Rooney, Hillsboro, OR (US); Hideki Shishido, Portland, OR (US); Zhongying Yang, Beaverton, OR (US)

(72) Inventors: William Skach, Portland, OR (US); LeeAnn Rooney, Hillsboro, OR (US); Hideki Shishido, Portland, OR (US); Zhongying Yang, Beaverton, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 143 days.

(21) Appl. No.: 14/050,177

(22) Filed: Oct. 9, 2013

(65) Prior Publication Data

US 2014/0099724 A1 Apr. 10, 2014

Related U.S. Application Data

(60) Provisional application No. 61/712,073, filed on Oct. 12, 2012.

(51) Int. Cl.
  *G01N 33/68* (2006.01)
  *G01N 21/64* (2006.01)
  *G01N 33/543* (2006.01)
  *G01N 33/542* (2006.01)

(52) U.S. Cl.
  CPC ........ *G01N 33/6803* (2013.01); *G01N 21/6428* (2013.01); *G01N 21/6486* (2013.01); *G01N 33/542* (2013.01); *G01N 33/543* (2013.01); *Y10T 436/13* (2015.01); *Y10T 436/143333* (2015.01); *Y10T 436/25125* (2015.01)

(58) Field of Classification Search
  CPC ... G01N 33/542; G01N 33/543; G01N 33/68; G01N 33/6803; G01N 21/64; G01N 21/6428; G01N 21/6486; Y10T 436/13; Y10T 436/143333; Y10T 436/25; Y10T 436/25125
  USPC .......... 436/56, 57, 86, 89, 94, 161, 164, 166, 436/172, 174, 175, 518, 524, 525, 531, 436/534; 422/430, 82.05, 82.08; 435/6.1, 435/6.13, 7.1, 7.8, 810, 975; 536/23.1
  See application file for complete search history.

(56) References Cited

U.S. PATENT DOCUMENTS

2010/0317116 A1* 12/2010 Flusberg et al. ................ 436/56
2010/0317121 A1* 12/2010 Smilansky ...................... 436/86

FOREIGN PATENT DOCUMENTS

WO  WO 2011/086116  7/2011

OTHER PUBLICATIONS

Saraogi et al. Journal of the American Chemical Society, vol. 133, 2011, pp. 14936-14939.*
A. Khushoo et al., "Ligand-Driven Vectorial Folding of Ribosome Bound Human CFTR NBD1", Molecular Cell, 41, pp. 682-692, Mar. 18, 2011.

* cited by examiner

*Primary Examiner* — Maureen Wallenhorst
(74) *Attorney, Agent, or Firm* — Jeffrey M. Jackson

(57) ABSTRACT

Disclosed herein are methods and kits useful in the detection of protein folding and in the identification of compounds that promote proper protein folding. In one example approach, fluorophores and a protein tag are incorporated into a nascent polypeptide within a ribosome-nascent-chain complex during cell free translation and the resulting labeled ribosome-nascent-chain complex is conjugated to a solid surface via the tag. Fluorescence imaging via FRET is then preformed to assess the folding state of the ribosome-nascent-chain complex under a variety of conditions.

21 Claims, 14 Drawing Sheets

His-tagged construct

Control construct with no His-tag

Beads alone

Scale bar= 100μm, Ex:430nm, Em:470nm

NET SIGNAL

14C CORRECTED

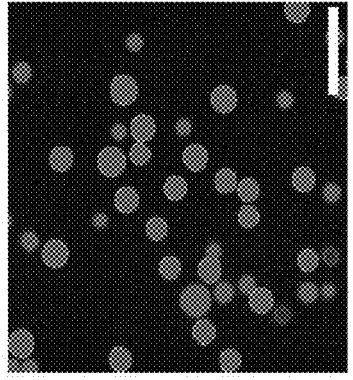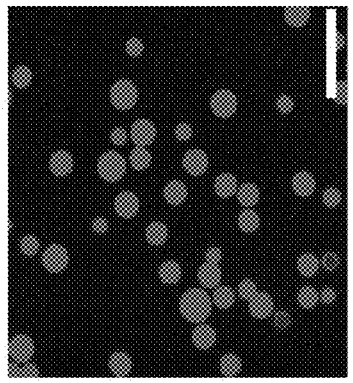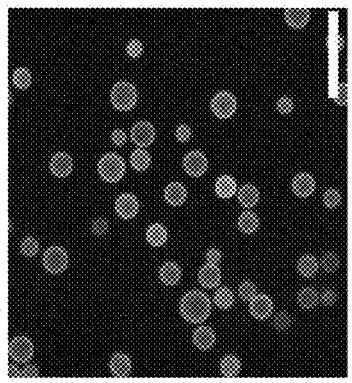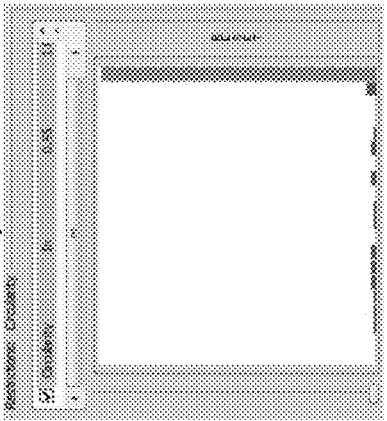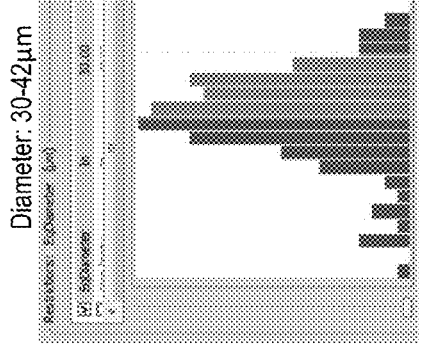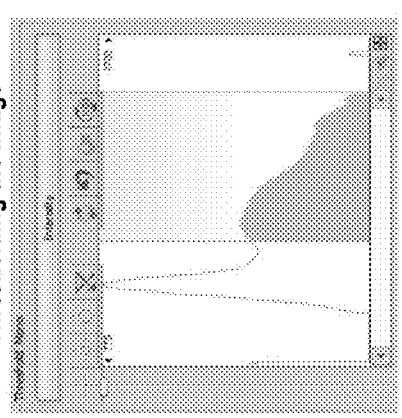
FIG. 20

FIG. 23
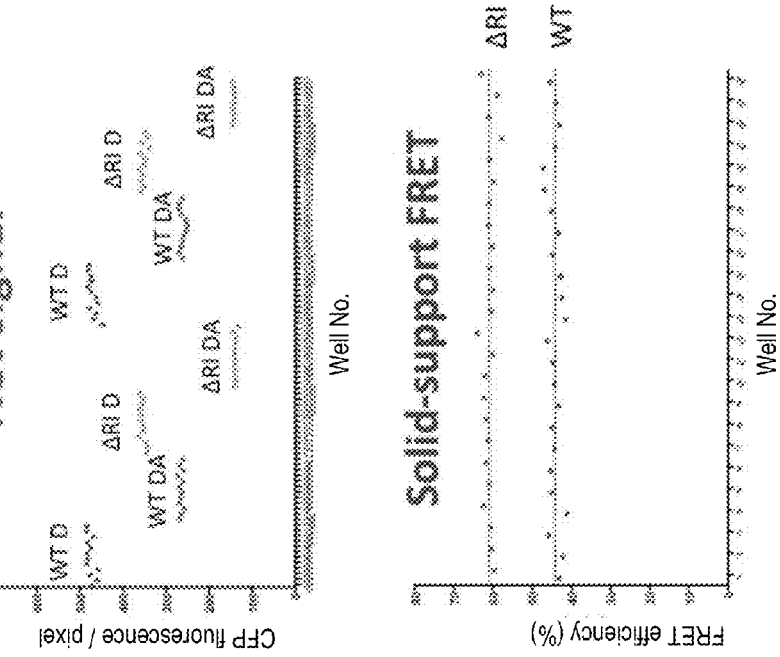
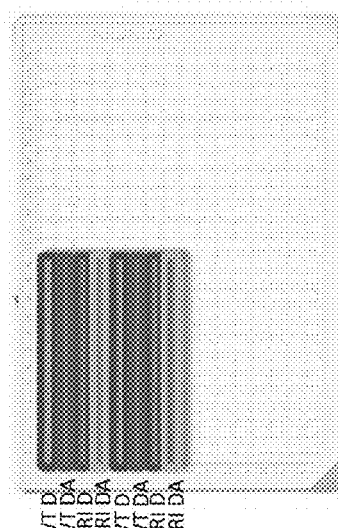
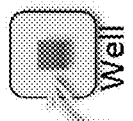
A
(Construct: R450TAG | 550V WT, and ΔRI)
384 well plate
500 beads / well
3sec x 4 pictures (12sec) / well
Frame size: 11% of well area
WT: 44.32% ± 1.6 (SD), N=24, CV%=3.6%
dRI: 61.0% ± 1.3 (SD), N=24, CV%=2.2%
Z factor = 0.5
Z-factor: $1 - \dfrac{3 \times (SD_P + SD_N)}{(Mean_P - Mean_N)}$  Positive cont: ΔRI
Negative cont: WT

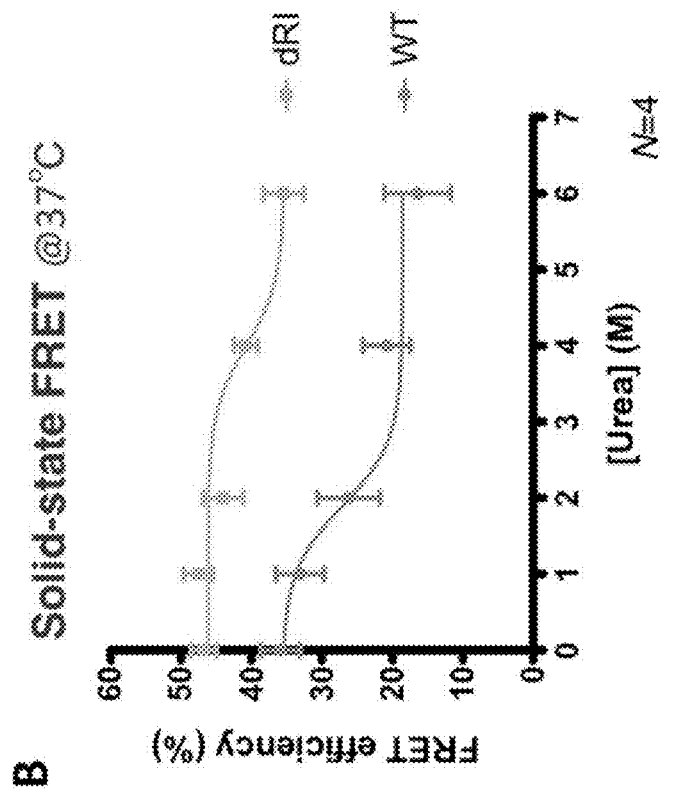
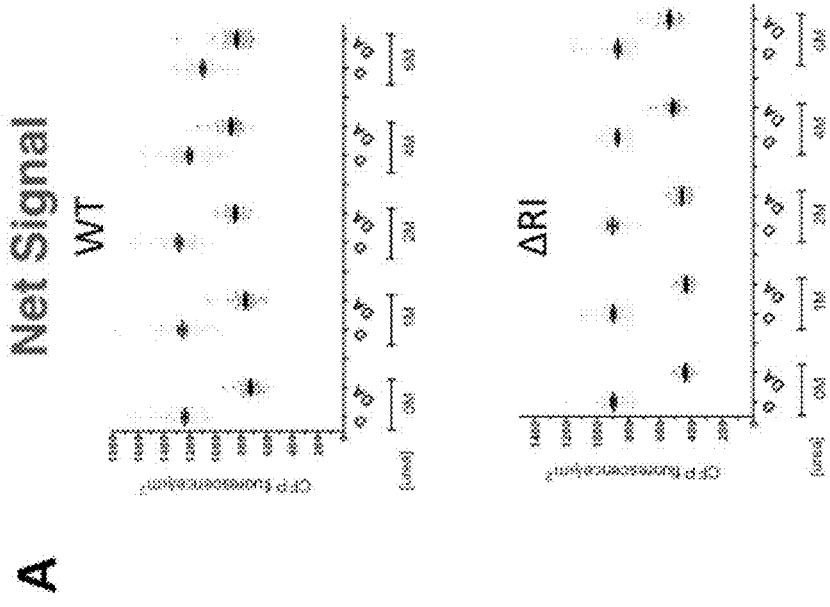
FIG. 24

SEQUENCE LISTING

<160> NUMBER OF SEQ ID NOS: 14

<210> SEQ ID NO 1
<211> LENGTH: 239
<212> TYPE: PRT
<213> ORGANISM: Artificial Sequence
<220> FEATURE:
<223> OTHER INFORMATION: Enhanced cyan fluorescent protein

<400> SEQUENCE: 1

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 2
<211> LENGTH: 356
<212> TYPE: PRT
<213> ORGANISM: Homo sapiens

<400> SEQUENCE: 2

Thr Thr Glu Val Val Met Glu Asn Val Thr Ala Phe Trp Glu Glu Gly

```
             1               5                  10                 15
      Phe Gly Glu Leu Phe Glu Lys Ala Lys Gln Asn Asn Asn Arg Lys
                     20                  25                 30

Thr Ser Asn Gly Asp Asp Ser Leu Phe Phe Ser Asn Phe Ser Leu Leu
              35                  40                 45

Gly Thr Pro Val Leu Lys Asp Ile Asn Phe Lys Ile Glu Arg Gly Gln
                  50                  55                 60

Leu Leu Ala Val Ala Gly Ser Thr Gly Ala Gly Lys Thr Ser Leu Leu
      65                  70                  75                 80

Met Met Ile Met Gly Glu Leu Glu Pro Ser Glu Gly Lys Ile Lys His
                          85                 90                 95

Ser Gly Arg Ile Ser Phe Cys Ser Gln Phe Ser Trp Ile Met Pro Gly
                      100                 105                110

Thr Ile Lys Glu Asn Ile Ile Phe Gly Val Ser Tyr Asp Glu Tyr Arg
                      115                 120                125

Tyr Arg Ser Val Ile Lys Ala Cys Gln Leu Glu Glu Asp Ile Ser Lys
                  130                 135                 140

Phe Ala Glu Lys Asp Asn Ile Val Leu Gly Glu Gly Ile Thr Leu
      145                 150                 155                 160

Ser Gly Gly Gln Arg Ala Arg Ile Ser Leu Ala Arg Ala Val Tyr Lys
                      165                 170                 175

Asp Ala Asp Leu Tyr Leu Leu Asp Ser Pro Phe Gly Tyr Leu Asp Val
                  180                 185                 190

Leu Thr Glu Lys Glu Ile Phe Glu Ser Cys Val Cys Lys Leu Met Ala
                  195                 200                 205

Asn Lys Thr Arg Ile Leu Val Thr Ser Lys Met Glu His Leu Lys Lys
                  210                 215                 220

Ala Asp Lys Ile Leu Ile Leu His Glu Gly Ser Ser Tyr Phe Tyr Gly
      225                 230                 235                 240

Thr Phe Ser Glu Leu Gln Asn Leu Gln Pro Asp Phe Ser Ser Lys Leu
                      245                 250                 255

Met Gly Cys Asp Ser Phe Asp Gln Phe Ser Ala Glu Arg Arg Asn Ser
                  260                 265                 270

Ile Leu Thr Glu Thr Leu His Arg Phe Ser Leu Glu Gly Asp Ala Pro
                  275                 280                 285

Val Ser Trp Thr Glu Thr Lys Lys Gln Ser Phe Lys Gln Thr Gly Glu
                  290                 295                 300

Phe Gly Glu Lys Arg Lys Asn Ser Ile Leu Asn Pro Ile Asn Ser Ile
      305                 310                 315                 320

Arg Lys Phe Ser Ile Val Gln Lys Thr Pro Leu Gln Met Asn Gly Ile
                      325                 330                 335

Glu Glu Asp Ser Asp Glu Pro Leu Glu Arg Arg Leu Ser Leu Val Pro
                  340                 345                 350

Asp Ser Glu Gln
                  355

<210> SEQ ID NO 3
<211> LENGTH: 57
<212> TYPE: PRT
<213> ORGANISM: Homo sapiens

<400> SEQUENCE: 3

Thr Thr Glu Val Val Met Glu Asn Val Thr Ala Phe Trp Glu Glu Gly
      1               5                  10                 15
```

-continued

Phe Gly Glu Leu Phe Glu Lys Ala Lys Gln Asn Asn Asn Arg Lys
            20                  25                  30

Thr Ser Asn Gly Asp Asp Ser Leu Phe Phe Ser Asn Phe Ser Leu Leu
        35                  40                  45

Gly Thr Pro Val Leu Lys Asp Ile Asn
    50                  55

<210> SEQ ID NO 4
<211> LENGTH: 62
<212> TYPE: PRT
<213> ORGANISM: Homo sapiens

<400> SEQUENCE: 4

Thr Thr Glu Val Val Met Glu Asn Val Thr Ala Phe Trp Glu Glu Gly
1               5                   10                  15

Phe Gly Glu Leu Phe Glu Lys Ala Lys Gln Asn Asn Asn Arg Lys
            20                  25                  30

Thr Ser Asn Gly Asp Asp Ser Leu Phe Phe Ser Asn Phe Ser Leu Leu
        35                  40                  45

Gly Thr Pro Val Leu Lys Asp Ile Asn Phe Lys Ile Glu Arg
    50                  55                  60

<210> SEQ ID NO 5
<211> LENGTH: 112
<212> TYPE: PRT
<213> ORGANISM: Homo sapiens

<400> SEQUENCE: 5

Thr Thr Glu Val Val Met Glu Asn Val Thr Ala Phe Trp Glu Glu Gly
1               5                   10                  15

Phe Gly Glu Leu Phe Glu Lys Ala Lys Gln Asn Asn Asn Arg Lys
            20                  25                  30

Thr Ser Asn Gly Asp Asp Ser Leu Phe Phe Ser Asn Phe Ser Leu Leu
        35                  40                  45

Gly Thr Pro Val Leu Lys Asp Ile Asn Phe Lys Ile Glu Arg Gly Gln
    50                  55                  60

Leu Leu Ala Val Ala Gly Ser Thr Gly Ala Gly Lys Thr Ser Leu Leu
65                  70                  75                  80

Met Met Ile Met Gly Glu Leu Glu Pro Ser Glu Gly Lys Ile Lys His
                85                  90                  95

Ser Gly Arg Ile Ser Phe Cys Ser Gln Phe Ser Trp Ile Met Pro Gly
            100                 105                 110

<210> SEQ ID NO 6
<211> LENGTH: 162
<212> TYPE: PRT
<213> ORGANISM: Homo sapiens

<400> SEQUENCE: 6

Thr Thr Glu Val Val Met Glu Asn Val Thr Ala Phe Trp Glu Glu Gly
1               5                   10                  15

Phe Gly Glu Leu Phe Glu Lys Ala Lys Gln Asn Asn Asn Arg Lys
            20                  25                  30

Thr Ser Asn Gly Asp Asp Ser Leu Phe Phe Ser Asn Phe Ser Leu Leu
        35                  40                  45

Gly Thr Pro Val Leu Lys Asp Ile Asn Phe Lys Ile Glu Arg Gly Gln
    50                  55                  60

Leu Leu Ala Val Ala Gly Ser Thr Gly Ala Gly Lys Thr Ser Leu Leu

```
                65                  70                  75                  80
Met Met Ile Met Gly Glu Leu Glu Pro Ser Glu Gly Lys Ile Lys His
                    85                  90                  95

Ser Gly Arg Ile Ser Phe Cys Ser Gln Phe Ser Trp Ile Met Pro Gly
                100                 105                 110

Thr Ile Lys Glu Asn Ile Ile Phe Gly Val Ser Tyr Asp Glu Tyr Arg
                115                 120                 125

Tyr Arg Ser Val Ile Lys Ala Cys Gln Leu Glu Glu Asp Ile Ser Lys
            130                 135                 140

Phe Ala Glu Lys Asp Asn Ile Val Leu Gly Glu Gly Ile Thr Leu
145                 150                 155                 160

Ser Gly

<210> SEQ ID NO 7
<211> LENGTH: 355
<212> TYPE: PRT
<213> ORGANISM: Homo sapiens

<400> SEQUENCE: 7

Thr Thr Glu Val Val Met Glu Asn Val Thr Ala Phe Trp Glu Glu Gly
1               5                   10                  15

Phe Gly Glu Leu Phe Glu Lys Ala Lys Gln Asn Asn Asn Asn Arg Lys
                20                  25                  30

Thr Ser Asn Gly Asp Asp Ser Leu Phe Phe Ser Asn Phe Ser Leu Leu
            35                  40                  45

Gly Thr Pro Val Leu Lys Asp Ile Asn Phe Lys Ile Glu Arg Gly Gln
        50                  55                  60

Leu Leu Ala Val Ala Gly Ser Thr Gly Ala Gly Lys Thr Ser Leu Leu
65                  70                  75                  80

Met Met Ile Met Gly Glu Leu Glu Pro Ser Glu Gly Lys Ile Lys His
                    85                  90                  95

Ser Gly Arg Ile Ser Phe Cys Ser Gln Phe Ser Trp Ile Met Pro Gly
                100                 105                 110

Thr Ile Lys Glu Asn Ile Ile Gly Val Ser Tyr Asp Glu Tyr Arg Tyr
                115                 120                 125

Arg Ser Val Ile Lys Ala Cys Gln Leu Glu Glu Asp Ile Ser Lys Phe
            130                 135                 140

Ala Glu Lys Asp Asn Ile Val Leu Gly Glu Gly Gly Ile Thr Leu Ser
145                 150                 155                 160

Gly Gly Gln Arg Ala Arg Ile Ser Leu Ala Arg Ala Val Tyr Lys Asp
                165                 170                 175

Ala Asp Leu Tyr Leu Leu Asp Ser Pro Phe Gly Tyr Leu Asp Val Leu
            180                 185                 190

Thr Glu Lys Glu Ile Phe Glu Ser Cys Val Cys Lys Leu Met Ala Asn
        195                 200                 205

Lys Thr Arg Ile Leu Val Thr Ser Lys Met Glu His Leu Lys Lys Ala
    210                 215                 220

Asp Lys Ile Leu Ile Leu His Glu Gly Ser Ser Tyr Phe Tyr Gly Thr
225                 230                 235                 240

Phe Ser Glu Leu Gln Asn Leu Gln Pro Asp Phe Ser Ser Lys Leu Met
                245                 250                 255

Gly Cys Asp Ser Phe Asp Gln Phe Ser Ala Glu Arg Arg Asn Ser Ile
                260                 265                 270

Leu Thr Glu Thr Leu His Arg Phe Ser Leu Glu Gly Asp Ala Pro Val
```

```
                275                 280                 285
Ser Trp Thr Glu Thr Lys Lys Gln Ser Phe Lys Gln Thr Gly Glu Phe
    290                 295                 300
Gly Glu Lys Arg Lys Asn Ser Ile Leu Asn Pro Ile Asn Ser Ile Arg
305                 310                 315                 320
Lys Phe Ser Ile Val Gln Lys Thr Pro Leu Gln Met Asn Gly Ile Glu
                325                 330                 335
Glu Asp Ser Asp Glu Pro Leu Gly Arg Arg Leu Ser Leu Val Pro Asp
            340                 345                 350
Ser Glu Gln
        355

<210> SEQ ID NO 8
<211> LENGTH: 161
<212> TYPE: PRT
<213> ORGANISM: Homo sapiens

<400> SEQUENCE: 8

Thr Thr Glu Val Val Met Glu Asn Val Thr Ala Phe Trp Glu Glu Gly
1               5                   10                  15
Phe Gly Glu Leu Phe Glu Lys Ala Lys Gln Asn Asn Asn Asn Arg Lys
                20                  25                  30
Thr Ser Asn Gly Asp Asp Ser Leu Phe Phe Ser Asn Phe Ser Leu Leu
            35                  40                  45
Gly Thr Pro Val Leu Lys Asp Ile Asn Phe Lys Ile Glu Arg Gly Gln
        50                  55                  60
Leu Leu Ala Val Ala Gly Ser Thr Gly Ala Gly Lys Thr Ser Leu Leu
65                  70                  75                  80
Met Met Ile Met Gly Glu Leu Glu Pro Ser Glu Gly Lys Ile Lys His
                85                  90                  95
Ser Gly Arg Ile Ser Phe Cys Ser Gln Phe Ser Trp Ile Met Pro Gly
                100                 105                 110
Thr Ile Lys Glu Asn Ile Ile Gly Val Ser Tyr Asp Glu Tyr Arg Tyr
            115                 120                 125
Arg Ser Val Ile Lys Ala Cys Gln Leu Glu Glu Asp Ile Ser Lys Phe
        130                 135                 140
Ala Glu Lys Asp Asn Ile Val Leu Gly Glu Gly Gly Ile Thr Leu Ser
145                 150                 155                 160
Gly

<210> SEQ ID NO 9
<211> LENGTH: 1479
<212> TYPE: PRT
<213> ORGANISM: Homo sapiens

<400> SEQUENCE: 9

Met Gln Arg Ser Pro Leu Glu Lys Ala Ser Val Val Ser Lys Leu Phe
1               5                   10                  15
Phe Ser Trp Thr Arg Pro Ile Leu Arg Lys Gly Tyr Arg Gln Arg Leu
                20                  25                  30
Glu Leu Ser Asp Ile Tyr Gln Ile Pro Ser Val Asp Ser Ala Asp Asn
            35                  40                  45
Leu Ser Glu Lys Leu Glu Arg Glu Trp Asp Arg Glu Leu Ala Ser Lys
        50                  55                  60
Lys Asn Pro Lys Leu Ile Asn Ala Leu Arg Arg Cys Phe Phe Trp Arg
65                  70                  75                  80
```

-continued

```
Phe Met Phe Tyr Gly Ile Phe Leu Tyr Leu Gly Val Thr Lys Ala
             85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
            130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
            210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
            290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
            370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495
```

```
Ile Met Pro Gly Thr Ile Lys Glu Asn Ile Ile Gly Val Ser Tyr Asp
            500                 505                 510
Glu Tyr Arg Tyr Arg Ser Val Ile Lys Ala Cys Gln Leu Glu Glu Asp
        515                 520                 525
Ile Ser Lys Phe Ala Glu Lys Asp Asn Ile Val Leu Gly Glu Gly Gly
    530                 535                 540
Ile Thr Leu Ser Gly Gly Gln Arg Ala Arg Ile Ser Leu Ala Arg Ala
545                 550                 555                 560
Val Tyr Lys Asp Ala Asp Leu Tyr Leu Leu Asp Ser Pro Phe Gly Tyr
            565                 570                 575
Leu Asp Val Leu Thr Glu Lys Glu Ile Phe Glu Ser Cys Val Cys Lys
        580                 585                 590
Leu Met Ala Asn Lys Thr Arg Ile Leu Val Thr Ser Lys Met Glu His
    595                 600                 605
Leu Lys Lys Ala Asp Lys Ile Leu Ile Leu His Glu Gly Ser Ser Tyr
610                 615                 620
Phe Tyr Gly Thr Phe Ser Glu Leu Gln Asn Leu Gln Pro Asp Phe Ser
            630                 635                 640
Ser Lys Leu Met Gly Cys Asp Ser Phe Asp Gln Phe Ser Ala Glu Arg
        645                 650                 655
Arg Asn Ser Ile Leu Thr Glu Thr Leu His Arg Phe Ser Leu Glu Gly
    660                 665                 670
Asp Ala Pro Val Ser Trp Thr Glu Thr Lys Lys Gln Ser Phe Lys Gln
675                 680                 685
Thr Gly Glu Phe Gly Glu Lys Arg Lys Asn Ser Ile Leu Asn Pro Ile
            690                 695                 700
Asn Ser Ile Arg Lys Phe Ser Ile Val Gln Lys Thr Pro Leu Gln Met
705                 710                 715                 720
Asn Gly Ile Glu Glu Asp Ser Asp Glu Pro Leu Glu Arg Arg Leu Ser
            725                 730                 735
Leu Val Pro Asp Ser Glu Gln Gly Glu Ala Ile Leu Pro Arg Ile Ser
        740                 745                 750
Val Ile Ser Thr Gly Pro Thr Leu Gln Ala Arg Arg Arg Gln Ser Val
    755                 760                 765
Leu Asn Leu Met Thr His Ser Val Asn Gln Gly Gln Asn Ile His Arg
770                 775                 780
Lys Thr Thr Ala Ser Thr Arg Lys Val Ser Leu Ala Pro Gln Ala Asn
785                 790                 795                 800
Leu Thr Glu Leu Asp Ile Tyr Ser Arg Arg Leu Ser Gln Glu Thr Gly
            805                 810                 815
Leu Glu Ile Ser Glu Glu Ile Asn Glu Glu Asp Leu Lys Glu Cys Phe
        820                 825                 830
Phe Asp Asp Met Glu Ser Ile Pro Ala Val Thr Thr Trp Asn Thr Tyr
    835                 840                 845
Leu Arg Tyr Ile Thr Val His Lys Ser Leu Ile Phe Val Leu Ile Trp
850                 855                 860
Cys Leu Val Ile Phe Leu Ala Glu Val Ala Ala Ser Leu Val Val Leu
865                 870                 875                 880
Trp Leu Leu Gly Asn Thr Pro Leu Gln Asp Lys Gly Asn Ser Thr His
            885                 890                 895
Ser Arg Asn Asn Ser Tyr Ala Val Ile Ile Thr Ser Thr Ser Ser Tyr
        900                 905                 910
Tyr Val Phe Tyr Ile Tyr Val Gly Val Ala Asp Thr Leu Leu Ala Met
```

-continued

```
            915                 920                 925
Gly Phe Phe Arg Gly Leu Pro Leu Val His Thr Leu Ile Thr Val Ser
        930                 935                 940
Lys Ile Leu His His Lys Met Leu His Ser Val Leu Gln Ala Pro Met
945                 950                 955                 960
Ser Thr Leu Asn Thr Leu Lys Ala Gly Gly Ile Leu Asn Arg Phe Ser
                965                 970                 975
Lys Asp Ile Ala Ile Leu Asp Asp Leu Leu Pro Leu Thr Ile Phe Asp
            980                 985                 990
Phe Ile Gln Leu Leu Leu Ile Val Ile Gly Ala Ile Ala Val Val Ala
            995                 1000                1005
Val Leu Gln Pro Tyr Ile Phe Val Ala Thr Val Pro Val Ile Val
    1010                1015                1020
Ala Phe Ile Met Leu Arg Ala Tyr Phe Leu Gln Thr Ser Gln Gln
    1025                1030                1035
Leu Lys Gln Leu Glu Ser Glu Gly Arg Ser Pro Ile Phe Thr His
    1040                1045                1050
Leu Val Thr Ser Leu Lys Gly Leu Trp Thr Leu Arg Ala Phe Gly
    1055                1060                1065
Arg Gln Pro Tyr Phe Glu Thr Leu Phe His Lys Ala Leu Asn Leu
    1070                1075                1080
His Thr Ala Asn Trp Phe Leu Tyr Leu Ser Thr Leu Arg Trp Phe
    1085                1090                1095
Gln Met Arg Ile Glu Met Ile Phe Val Ile Phe Ile Ala Val
    1100                1105                1110
Thr Phe Ile Ser Ile Leu Thr Thr Gly Glu Gly Glu Gly Arg Val
    1115                1120                1125
Gly Ile Ile Leu Thr Leu Ala Met Asn Ile Met Ser Thr Leu Gln
    1130                1135                1140
Trp Ala Val Asn Ser Ser Ile Asp Val Asp Ser Leu Met Arg Ser
    1145                1150                1155
Val Ser Arg Val Phe Lys Phe Ile Asp Met Pro Thr Glu Gly Lys
    1160                1165                1170
Pro Thr Lys Ser Thr Lys Pro Tyr Lys Asn Gly Gln Leu Ser Lys
    1175                1180                1185
Val Met Ile Ile Glu Asn Ser His Val Lys Lys Asp Asp Ile Trp
    1190                1195                1200
Pro Ser Gly Gly Gln Met Thr Val Lys Asp Leu Thr Ala Lys Tyr
    1205                1210                1215
Thr Glu Gly Gly Asn Ala Ile Leu Glu Asn Ile Ser Phe Ser Ile
    1220                1225                1230
Ser Pro Gly Gln Arg Val Gly Leu Leu Gly Arg Thr Gly Ser Gly
    1235                1240                1245
Lys Ser Thr Leu Leu Ser Ala Phe Leu Arg Leu Leu Asn Thr Glu
    1250                1255                1260
Gly Glu Ile Gln Ile Asp Gly Val Ser Trp Asp Ser Ile Thr Leu
    1265                1270                1275
Gln Gln Trp Arg Lys Ala Phe Gly Val Ile Pro Gln Lys Val Phe
    1280                1285                1290
Ile Phe Ser Gly Thr Phe Arg Lys Asn Leu Asp Pro Tyr Glu Gln
    1295                1300                1305
Trp Ser Asp Gln Glu Ile Trp Lys Val Ala Asp Glu Val Gly Leu
    1310                1315                1320
```

Arg Ser Val Ile Glu Gln Phe Pro Gly Lys Leu Asp Phe Val Leu
1325             1330             1335

Val Asp Gly Gly Cys Val Leu Ser His Gly His Lys Gln Leu Met
1340             1345             1350

Cys Leu Ala Arg Ser Val Leu Ser Lys Ala Lys Ile Leu Leu Leu
1355             1360             1365

Asp Glu Pro Ser Ala His Leu Asp Pro Val Thr Tyr Gln Ile Ile
1370             1375             1380

Arg Arg Thr Leu Lys Gln Ala Phe Ala Asp Cys Thr Val Ile Leu
1385             1390             1395

Cys Glu His Arg Ile Glu Ala Met Leu Glu Cys Gln Gln Phe Leu
1400             1405             1410

Val Ile Glu Glu Asn Lys Val Arg Gln Tyr Asp Ser Ile Gln Lys
1415             1420             1425

Leu Leu Asn Glu Arg Ser Leu Phe Arg Gln Ala Ile Ser Pro Ser
1430             1435             1440

Asp Arg Val Lys Leu Phe Pro His Arg Asn Ser Ser Lys Cys Lys
1445             1450             1455

Ser Lys Pro Gln Ile Ala Ala Leu Lys Glu Glu Thr Glu Glu Glu
1460             1465             1470

Val Gln Asp Thr Arg Leu
1475

<210> SEQ ID NO 10
<211> LENGTH: 1479
<212> TYPE: PRT
<213> ORGANISM: Homo sapiens

<400> SEQUENCE: 10

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val

```
              195                 200                 205
Ala Leu Leu Met Gly Leu Ile Trp Glu Leu Leu Gln Ala Ser Ala Phe
210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                    245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
        290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                    325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                    405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
        450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                    485                 490                 495

Ile Met Pro Gly Thr Ile Lys Glu Asn Ile Ile Gly Val Ser Tyr Asp
                500                 505                 510

Glu Tyr Arg Tyr Arg Ser Val Ile Lys Ala Cys Gln Leu Glu Glu Asp
            515                 520                 525

Ile Ser Lys Phe Ala Glu Lys Asp Asn Ile Val Leu Gly Glu Gly Gly
        530                 535                 540

Ile Thr Leu Ser Gly Gly Gln Arg Ala Arg Ile Ser Leu Ala Arg Ala
545                 550                 555                 560

Val Tyr Lys Asp Ala Asp Leu Tyr Leu Leu Asp Ser Pro Phe Gly Tyr
                    565                 570                 575

Leu Asp Val Leu Thr Glu Lys Glu Ile Phe Glu Ser Cys Val Cys Lys
                580                 585                 590

Leu Met Ala Asn Lys Thr Arg Ile Leu Val Thr Ser Lys Met Glu His
            595                 600                 605

Leu Lys Lys Ala Asp Lys Ile Leu Ile Leu His Glu Gly Ser Ser Tyr
        610                 615                 620
```

-continued

Phe Tyr Gly Thr Phe Ser Glu Leu Gln Asn Leu Gln Pro Asp Phe Ser
625                 630                 635                 640

Ser Lys Leu Met Gly Cys Asp Ser Phe Asp Gln Phe Ser Ala Glu Arg
            645                 650                 655

Arg Asn Ser Ile Leu Thr Glu Thr Leu His Arg Phe Ser Leu Glu Gly
            660                 665                 670

Asp Ala Pro Val Ser Trp Thr Glu Thr Lys Lys Gln Ser Phe Lys Gln
            675                 680                 685

Thr Gly Glu Phe Gly Glu Lys Arg Lys Asn Ser Ile Leu Asn Pro Ile
690                 695                 700

Asn Ser Ile Arg Lys Phe Ser Ile Val Gln Lys Thr Pro Leu Gln Met
705                 710                 715                 720

Asn Gly Ile Glu Glu Asp Ser Asp Glu Pro Leu Glu Arg Arg Leu Ser
            725                 730                 735

Leu Val Pro Asp Ser Glu Gln Gly Glu Ala Ile Leu Pro Arg Ile Ser
            740                 745                 750

Val Ile Ser Thr Gly Pro Thr Leu Gln Ala Arg Arg Gln Ser Val
            755                 760                 765

Leu Asn Leu Met Thr His Ser Val Asn Gln Gly Gln Asn Ile His Arg
770                 775                 780

Lys Thr Thr Ala Ser Thr Arg Lys Val Ser Leu Ala Pro Gln Ala Asn
785                 790                 795                 800

Leu Thr Glu Leu Asp Ile Tyr Ser Arg Arg Leu Ser Gln Glu Thr Gly
            805                 810                 815

Leu Glu Ile Ser Glu Glu Ile Asn Glu Asp Leu Lys Glu Cys Phe
            820                 825                 830

Phe Asp Asp Met Glu Ser Ile Pro Ala Val Thr Thr Trp Asn Thr Tyr
835                 840                 845

Leu Arg Tyr Ile Thr Val His Lys Ser Leu Ile Phe Val Leu Ile Trp
850                 855                 860

Cys Leu Val Ile Phe Leu Ala Glu Val Ala Ala Ser Leu Val Val Leu
865                 870                 875                 880

Trp Leu Leu Gly Asn Thr Pro Leu Gln Asp Lys Gly Asn Ser Thr His
            885                 890                 895

Ser Arg Asn Asn Ser Tyr Ala Val Ile Ile Thr Ser Thr Ser Ser Tyr
            900                 905                 910

Tyr Val Phe Tyr Ile Tyr Val Gly Val Ala Asp Thr Leu Leu Ala Met
            915                 920                 925

Gly Phe Phe Arg Gly Leu Pro Leu Val His Thr Leu Ile Thr Val Ser
            930                 935                 940

Lys Ile Leu His His Lys Met Leu His Ser Val Leu Gln Ala Pro Met
945                 950                 955                 960

Ser Thr Leu Asn Thr Leu Lys Ala Gly Gly Ile Leu Asn Arg Phe Ser
            965                 970                 975

Lys Asp Ile Ala Ile Leu Asp Asp Leu Pro Leu Thr Ile Phe Asp
            980                 985                 990

Phe Ile Gln Leu Leu Leu Ile Val  Ile Gly Ala Ile Ala  Val Val Ala
            995                 1000                1005

Val Leu  Gln Pro Tyr Ile Phe  Val Ala Thr Val Pro  Val Ile Val
    1010                1015                1020

Ala Phe Ile Met Leu Arg Ala  Tyr Phe Leu Gln Thr  Ser Gln Gln
    1025                1030                1035

```
Leu Lys Gln Leu Glu Ser Glu Gly Arg Ser Pro Ile Phe Thr His
1040                1045                1050

Leu Val Thr Ser Leu Lys Gly Leu Trp Thr Leu Arg Ala Phe Gly
1055                1060                1065

Arg Gln Pro Tyr Phe Glu Thr Leu Phe His Lys Ala Leu Asn Leu
1070                1075                1080

His Thr Ala Asn Trp Phe Leu Tyr Leu Ser Thr Leu Arg Trp Phe
1085                1090                1095

Gln Met Arg Ile Glu Met Ile Phe Val Ile Phe Phe Ile Ala Val
1100                1105                1110

Thr Phe Ile Ser Ile Leu Thr Thr Gly Glu Gly Glu Gly Arg Val
1115                1120                1125

Gly Ile Ile Leu Thr Leu Ala Met Asn Ile Met Ser Thr Leu Gln
1130                1135                1140

Trp Ala Val Asn Ser Ser Ile Asp Val Asp Ser Leu Met Arg Ser
1145                1150                1155

Val Ser Arg Val Phe Lys Phe Ile Asp Met Pro Thr Glu Gly Lys
1160                1165                1170

Pro Thr Lys Ser Thr Lys Pro Tyr Lys Asn Gly Gln Leu Ser Lys
1175                1180                1185

Val Met Ile Ile Glu Asn Ser His Val Lys Lys Asp Asp Ile Trp
1190                1195                1200

Pro Ser Gly Gly Gln Met Thr Val Lys Asp Leu Thr Ala Lys Tyr
1205                1210                1215

Thr Glu Gly Gly Asn Ala Ile Leu Glu Asn Ile Ser Phe Ser Ile
1220                1225                1230

Ser Pro Gly Gln Arg Val Gly Leu Leu Gly Arg Thr Gly Ser Gly
1235                1240                1245

Lys Ser Thr Leu Leu Ser Ala Phe Leu Arg Leu Leu Asn Thr Glu
1250                1255                1260

Gly Glu Ile Gln Ile Asp Gly Val Ser Trp Asp Ser Ile Thr Leu
1265                1270                1275

Gln Gln Trp Arg Lys Ala Phe Gly Val Ile Pro Gln Lys Val Phe
1280                1285                1290

Ile Phe Ser Gly Thr Phe Arg Lys Asn Leu Asp Pro Tyr Glu Gln
1295                1300                1305

Trp Ser Asp Gln Glu Ile Trp Lys Val Ala Asp Glu Val Gly Leu
1310                1315                1320

Arg Ser Val Ile Glu Gln Phe Pro Gly Lys Leu Asp Phe Val Leu
1325                1330                1335

Val Asp Gly Gly Cys Val Leu Ser His Gly His Lys Gln Leu Met
1340                1345                1350

Cys Leu Ala Arg Ser Val Leu Ser Lys Ala Lys Ile Leu Leu Leu
1355                1360                1365

Asp Glu Pro Ser Ala His Leu Asp Pro Val Thr Tyr Gln Ile Ile
1370                1375                1380

Arg Arg Thr Leu Lys Gln Ala Phe Ala Asp Cys Thr Val Ile Leu
1385                1390                1395

Cys Glu His Arg Ile Glu Ala Met Leu Glu Cys Gln Gln Phe Leu
1400                1405                1410

Val Ile Glu Glu Asn Lys Val Arg Gln Tyr Asp Ser Ile Gln Lys
1415                1420                1425

Leu Leu Asn Glu Arg Ser Leu Phe Arg Gln Ala Ile Ser Pro Ser
```

```
                1430              1435              1440
Asp Arg Val Lys Leu Phe Pro His Arg Asn Ser Ser Lys Cys Lys
        1445              1450              1455

Ser Lys Pro Gln Ile Ala Ala Leu Lys Glu Glu Thr Glu Glu Glu
        1460              1465              1470

Val Gln Asp Thr Arg Leu
        1475

<210> SEQ ID NO 11
<211> LENGTH: 10
<212> TYPE: PRT
<213> ORGANISM: Artificial Sequence
<220> FEATURE:
<223> OTHER INFORMATION: His-tag

<400> SEQUENCE: 11

His His His His His His His His His His
1               5                   10

<210> SEQ ID NO 12
<211> LENGTH: 30
<212> TYPE: DNA
<213> ORGANISM: Artificial Sequence
<220> FEATURE:
<223> OTHER INFORMATION: His tag

<400> SEQUENCE: 12
catcaccatc accatcacca tcaccatcac                                  30

<210> SEQ ID NO 13
<211> LENGTH: 21
<212> TYPE: PRT
<213> ORGANISM: Artificial Sequence
<220> FEATURE:
<223> OTHER INFORMATION: Linker sequence

<400> SEQUENCE: 13

Ser Gly Gly Ser Gly Gly Ser Gly Gly Ser Gly Gly Ser Gly Gly Ser
1               5                   10                  15

Gly Gly Ser Gly Gly
            20

<210> SEQ ID NO 14
<211> LENGTH: 63
<212> TYPE: DNA
<213> ORGANISM: Artificial Sequence
<220> FEATURE:
<223> OTHER INFORMATION: Linker molecule

<400> SEQUENCE: 14
gaaggtagcg gcggtagtgg aggctctggt gggtcaggcg gatccggtgg atcgggaggt    60
tcg                                                                 63
```

FLUORESCENT DETECTION OF IN VITRO TRANSLATED PROTEIN ON A SOLID SURFACE

CROSS-REFERENCE TO RELATED APPLICATION

This application claims priority from U.S. Provisional Patent Application Ser. No. 61/712,073, filed on 10 Oct. 2012, the entirety of which is hereby incorporated herein by reference for all purposes.

ACKNOWLEDGEMENT OF GOVERNMENT SUPPORT

This invention was made with the support of the United States government under grant numbers GM53457 and DK51818, both of which were awarded by the National Institutes of Health. The United States government has certain rights in these inventions.

BACKGROUND

Biochemical screens for small molecules that correct protein misfolding currently require large amounts of well-behaved, pure protein. Such screens are time consuming, expensive, limited to soluble pre-folded substrates, and lack the capacity to access intermediate folding states that may be defective in protein folding disorders.

One example of such a screen is a screen for small molecules that corrects misfolding and subsequent degradation of CFTR proteins. One common mutation in cystic fibrosis patients is a deletion of the phenylalanine at amino acid position 508. This mutation is referred to in the art and herein as ΔF508 CFTR. F508 is located in the first nucleotide binding domain (NBD1) of CFTR. The ΔF508 mutation has detrimental effects on the folding efficiency of the NBD1 in cells, and on the thermodynamic stability of NBD1 in vitro. The efficiency of NBD1 folding is a limiting factor in CFTR trafficking, which is further compromised by the ΔF508 mutation.

An important goal in cystic fibrosis (CF) therapeutics, therefore, is to understand how the NBD1 domain acquires and maintains its folded state in the cellular environment and to devise pharmacological strategies to improve folding efficiency. Clearly, methods that allow more efficient study of protein folding and that identify compounds that improve the folding efficiency of the NBD1 domain and other misfolded proteins that cause disease are needed.

As described in Khushoo et al, Mol Cell 41, 682-692 (2011), the entirety of which is hereby incorporated herein by reference for all purposes, FRET-based methods can be used in cell free translation systems to define the NBD1 folding pathway and showed that cotranslational NBD1 folding begins with compaction of the N-terminal ATP-binding subdomain, followed by alpha-subdomain folding and lastly, formation of the central α/β-sheet core. Thus, the ability to monitor folding directly on the ribosome is desirable because it allows access to folding intermediates that exist only transiently during translation.

However, while cell free translation systems enable quantitative incorporation of fluorescent probes, the concentration of proteins obtained from stalled ribosomes is exceedingly low (e.g., approximately 1 nM). This poses significant challenges to identifying small molecules that might promote protein stability and/or folding efficiency.

SUMMARY

In order to address the above-described issues, methods and kits for monitoring protein folding directly on the ribosome using a solid-state system to immobilize tagged ribosome-nascent-chain complexes (RNCs) on a solid support are disclosed. For example, fluorophores, e.g., an appropriate FRET donor and acceptor pair, and a protein tag (such as a His-tag) may be incorporated into an RNC during translation and the resulting labeled RNC can be conjugated to a solid surface comprising an agent that specifically binds a protein tag. For example, an RNC comprising a His-tag can be conjugated to a solid substrate such as an agarose bead, plate, or array comprising a metal matrix such as a nickel matrix. Fluorescence imaging via FRET may then be used to assess the folding state of the RNC under a variety of conditions.

Such an approach may be used to perform rapid high throughput screens to identify small molecule compounds that alter protein structure and/or folding during cotranslational synthesis. In particular, such an approach may be used to provide access to transient folding intermediates by the capture of the substrate at defined stages of the folding pathway to access ribosome-bound folding intermediates. Accessing ribosome-bound folding intermediates provides the potential to identify unique small molecules that act on the folding pathway and deter off-pathway reactions, in addition to those that stabilize the native folded state.

Further, fluorescence spectroscopy of immobilized nascent polypeptides improves sensitivity of folding readout by several orders of magnitude as compared with previous approaches so that it is now possible to measure folding using only several million molecules, thus allowing tens of thousands of measurements to be made using the same amount of total material previously used for a single measurement. For example, such an approach may be used to rapidly generate cotranslational folding intermediates whose structure can be assessed on attomolar and potentially sub-attomolar ($10^{-16}$-$10^{-18}$ mole) quantities in the ribosome attached state.

Such an approach eliminates the need for highly sensitive steady state fluorescence measurements and greatly simplifies data acquisition since the analysis is performed on a substrate concentrated on a solid support rather than in solution. In such an approach, the optical readout using microscopy can be scaled to acquire data several orders of magnitude more rapidly in an automated platform that is well suited to a high throughput format. Further such an approach may decrease time and costs associated with sample preparation. In particular, in vitro expression of protein substrates eliminates costly and time consuming large scale protein purification protocols. For example, samples sufficient for tens of thousands of measurements can be generated in about 2-3 hours.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 20 shows raw image of beads containing immobilized His-CFP-NBD1 obtained using Nikon Ti-E eclipse microscope with Lumencor Sola Light Engine and Andoryla Camera [excitation wavelength, 436 nm (426-446 nm), emission wavelength, 480 nm (460-500 nm)]. Beads were identified by thresholding the image based on pixel density histogram, and images were processed by applying software operations to the image such as Smooth (smooths the binary image contours), Fill Holes (fills holes within binary objects), and Separate (separates objects). Unfocused beads are eliminated by applying restrictions of diameter and circularity. Average image intensity of beads which meet acceptable parameters is exported for analysis and FRET calculations.

FIGS. 23A-23C show experimental design (panel A), and FRET results (Panels B and C) for the wild type and RI deletion mutant ribosome bound His-CFP-NBD1 containing the acceptor probe at residue 450 and truncated at residue 550. Beads from each construct containing donor or donor plus acceptor probes were placed in 24 wells of a 384 well plate and images were captured as described in FIG. 21. Panel B shows plots of net fluorescence for each well, while panel C shows the calculated FRET values for wild type and RI deletion polypeptides. This data was used to calculate a Z-factor using the formula shown ov 0.5 which indicates a robust assay suitable for screening purposes. For both constructs the coefficient of variance (calculated as Mean/SD×100) was <10%, again showing excellent well-to well reproducibility.

FIGS. 24A-24B show that solid support FRET is able to detect chemically induced unfolding of NBD1 using urea denaturation in a 96 well plate. Panel A shows net fluorescence intensity of beads containing wild type and ΔRI constructs (His-CFP-NBD1 with acceptor probe inserted at residue Arg450 and truncated at residue 550) in urea concentrations ranging from 0 to 6 M. Panel B shows graph of FRET versus urea concentration where the decrease in FRET indicates unfolding of the domain. This data demonstrates that the solid support FRET assay can detect different stabilities of wild type and mutant domains in a high throughput screening format

SEQUENCE LISTING

SEQ ID NO: 1 is an amino acid sequence of enhanced cyan fluorescent protein.

SEQ ID NO: 2 is an amino acid sequence of nucleotide binding domain 1 (NBD1) of CTFR.

Figure 3:
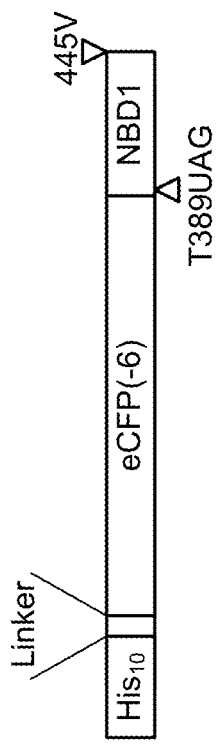
FIG. 3 schematically shows a ribosome-bound CFP-NBD1 nascent polypeptide with an N-terminal His-tag and an acceptor probe incorporated at a UAG translational stop codon at residue Thr389 of CFTR and truncated at CFTR residue 445.

SEQ ID NO: 3 is an amino acid sequence of NBD1 truncated at 445 amino acids (See FIG. 3).

Figure 7:
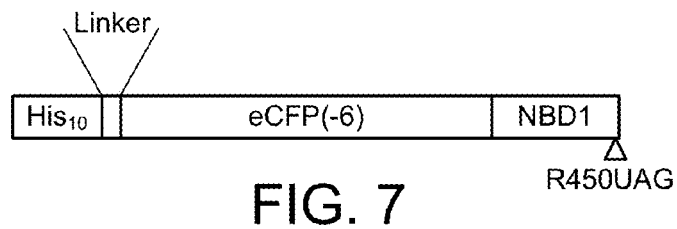
FIG. 7 schematically shows an in vitro synthesized CFP-NBD1 polypeptide with an N-terminal His-tag and an acceptor probe incorporated at Arg450.

SEQ ID NO: 4 is an amino acid sequence of NBD1 truncated at 450 amino acids (See FIG. 7).

Figure 10:
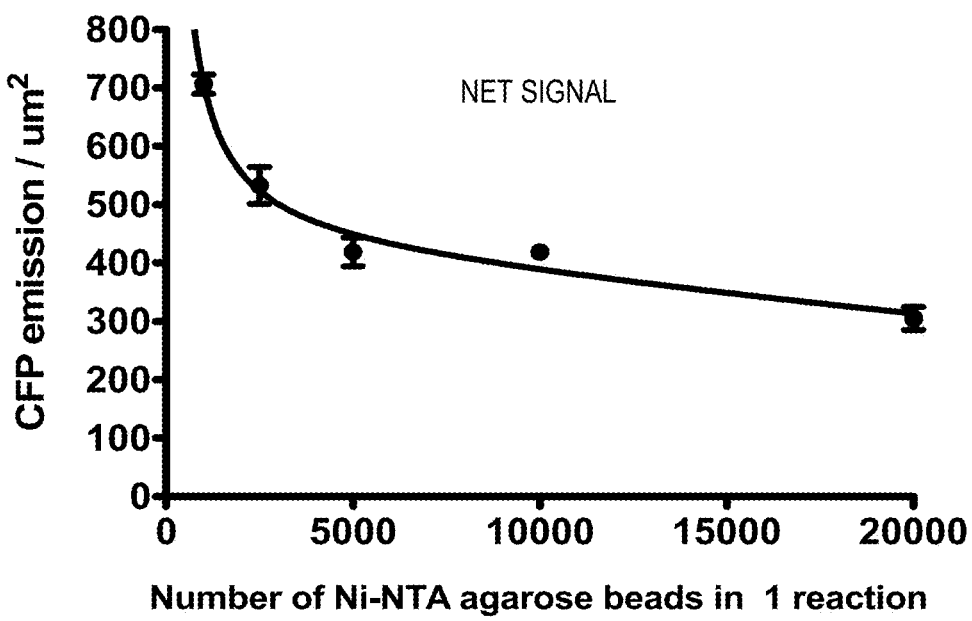
FIG. 10 shows a graph of CFP fluorescence intensity of bound CFP-NBD1 versus the number of agarose beads in one binding reaction containing ribosome-bound CFP-NBD1 nascent polypeptides with N-terminal His-tags and truncated at CFTR residue 500.
Figure 11:
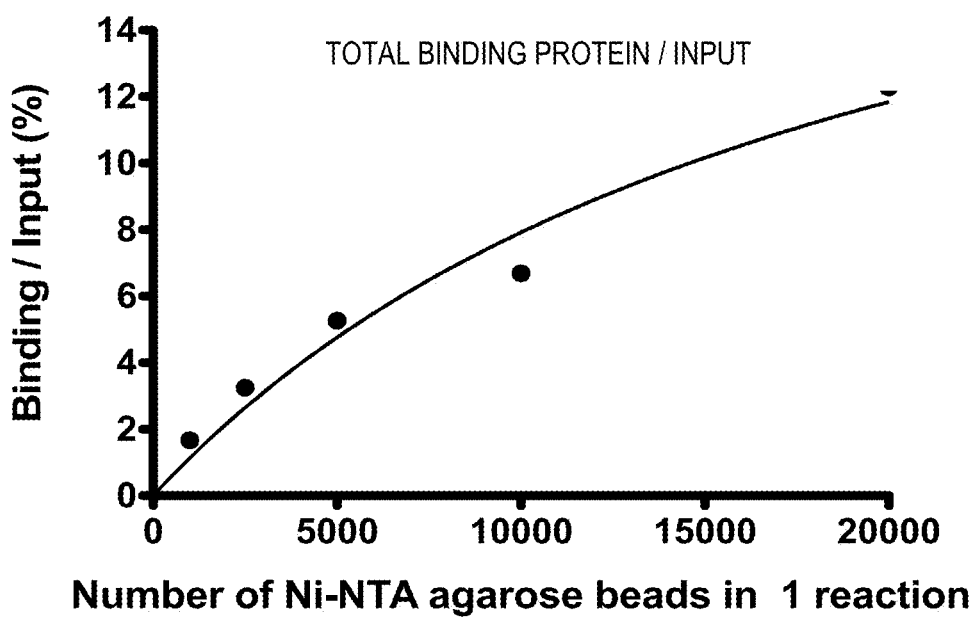
FIG. 11 shows a graph of binding efficiency (binding/input) versus the number of agarose beads in one binding reaction with ribosome-bound CFP-NBD1 nascent polypeptides with N-terminal His-tags and acceptor probes incorporated at Thr389 and truncated at CFTR residue 500.
Figure 17:
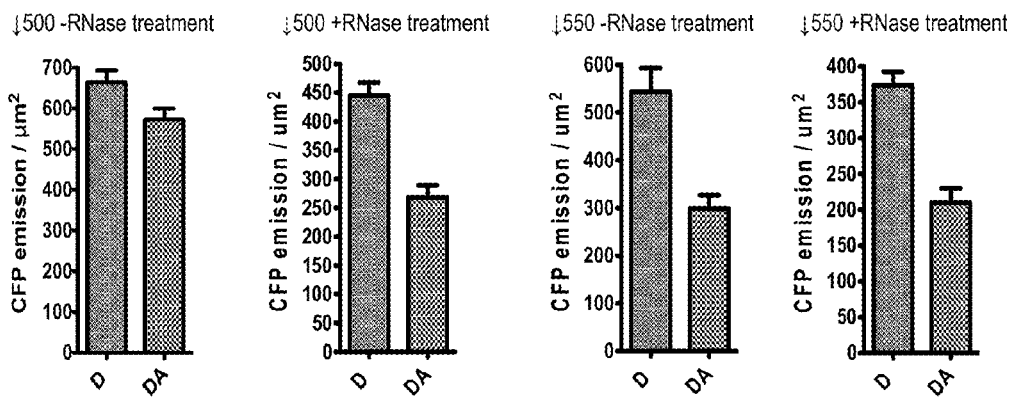
FIG. 17 shows graphs with plots of CFP emission of agarose bead-bound CFP-NBD1 nascent polypeptides with N-terminal His-tags and acceptor probes incorporated at Arg450 and truncated at CFTR residues 500 and 550 which are bound to ribosomes and released from ribosomes via treatment with RNase.

SEQ ID NO: 5 is an amino acid sequence of NBD1 truncated at 500 amino acids (See FIG. 10 and FIG. 17).

Figure 5:
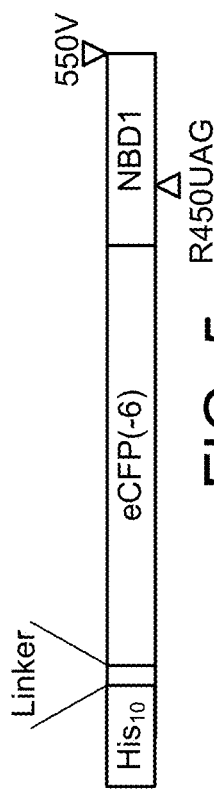
FIG. 5 schematically shows a ribosome-bound CFP-NBD1 nascent polypeptide with an N-terminal His-tag and an acceptor probe incorporated at Arg450 and truncated at CFTR residue 550.
Figure 13:
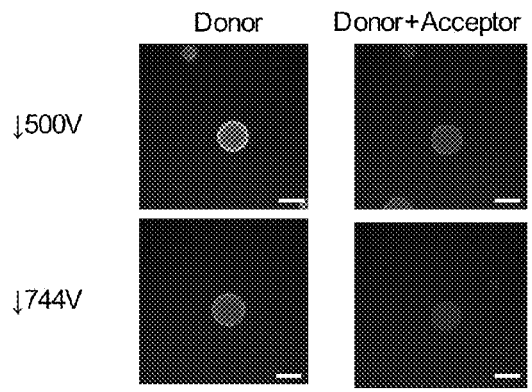
FIG. 13 shows example fluorescence micrographs obtained from agarose bead-bound and ribosome-bound CFP-NBD1 nascent polypeptides truncated at CFTR residues 500 and 744 with only the CFP donor incorporated and with both a CFP donor and an acceptor probe incorporated at residue Thr389.

SEQ ID NO: 6 is an amino acid sequence of NBD1 truncated at 550 amino acids (See FIG. 5, FIG. 13, and FIG. 17).

SEQ ID NO: 7 is an amino acid sequence of the first nucleotide binding domain of CFTR (SEQ ID NO: 2) with a ΔF508 mutation.

SEQ ID NO: 8 is an amino acid sequence of the first nucleotide binding domain of CFTR (SEQ ID NO: 2) with a ΔF508 mutation truncated to 550 amino acids.

SEQ ID NO: 9 is an amino acid sequence of full length CTFR.

SEQ ID NO: 10 is an amino acid sequence full length CTFR ΔF508.

SEQ ID NO: 11 is the amino acid sequence of a His-tag.

SEQ ID NO: 12 is a nucleic acid sequence that encodes the His-tag of SEQ ID NO: 11

SEQ ID NO: 13 is the amino acid sequence of a flexible linker molecule.

SEQ ID NO: 14 is a nucleic acid sequence that encodes the flexible linker molecule of SEQ ID NO: 13.

DETAILED DESCRIPTION

Terms

The following terms are described in this section solely to facilitate review of the disclosure.

CFTR: Cystic fibrosis transmembrane conductance regulator (CFTR) is a protein that in humans is encoded by the CFTR gene. The CFTR gene, found at the q31.2 locus of chromosome 7, is 230,000 base pairs long, and creates a protein that is 1,480 amino acids long. More specifically the location is between base 117,120,016 to 117,308,718 on the long arm of chromosome 7, region 3, band 1, sub-band 2, represented as 7q31.2. Structurally, CFTR is a type of gene known as an ABC gene. The product of this gene (the CFTR) is a chloride ion channel important in creating sweat, digestive juices and mucus. This protein possesses two ATP-hydrolyzing domains, which allows the protein to use energy in the form of ATP. It also contains two domains comprising 6 alpha helices apiece, which allow the protein to reside within the cell membrane. A regulatory domain (or region) on the protein allows activation by phosphorylation, mainly by cAMP-dependent protein kinase. The carboxyl terminal of the protein is anchored to the cytoskeleton by a PDZ domain interaction.

Domain: A domain of a polypeptide or protein may be any part of a protein that exhibits a particular defined structure and/or mediates a particular protein function. An example of a domain includes the first nucleotide binding domain (NBD1) of CFTR.

NBD1: the first nucleotide binding domain of CFTR.

RNC: A ribosome nascent chain complex (RNC) is the collection of molecules comprising a ribosome and a polypeptide that it is synthesizing.

Protein folding: The process by which a protein structure assumes its functional shape or conformation. It is the physical process by which a polypeptide folds into its characteristic and functional three-dimensional structure from random coil.

FRET: FRET (Fluorescence Resonance Energy Transfer or Förster Resonance Energy Transfer) is a distance dependent transfer of energy from a donor molecule to an acceptor molecule. The donor molecule can be any dye, chromophore, or fluorescent molecule that can absorb energy in the form of a visible or invisible light photon. The acceptor can be any other dye, chromophore or fluorescent compound that can receive the energy from the donor. The interaction occurs at a distance greater than atomic distance and results in a reduction in the donor molecule's fluorescent intensity and excited state lifetime and an increase in the excited state energy of the acceptor. A pair of molecules that interact in such a way such that FRET occurs may be referred to as a donor-acceptor pair.

For FRET to occur, the donor and acceptor need to be in close proximity to one another (generally between 10-100 Å depending on the identity of the donor-acceptor pair.) Furthermore, the absorption or excitation spectrum of the acceptor should overlap the fluorescence emission spectrum of the donor. The degree of overlap can be referred to as the spectral overlap integral (J) and the donor and acceptor dipoles should be approximately parallel.

FRET provides a useful tool to monitor conformational changes on a macromolecular scale that are typically associated with protein folding, structural dynamics, and chaperone interaction. FRET involves the transfer of excited state energy from a donor fluorophore to an acceptor fluorophore (or chromophore) without emission of a photon. Because FRET efficiency (EFRET) is highly dependent on the distance (R) between the donor and acceptor probes (EFRET=$R_0^6/(R_0^6+R^6)$) where $R_0$ is the Förster distance at which EFRET is 50%), it can readily distinguish structural changes that take place as a protein folds from an extended conformation to a compact tertiary structure.

Label: A label may be any substance capable of aiding a machine, detector, sensor, device, column, or enhanced or unenhanced human eye from differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism. Examples of labels include but are not limited to: radioactive isotopes (such as carbon-14 or $^{14}C$) or chelates thereof; dyes (fluorescent or nonfluorescent), stains, enzymes, nonradioactive metals, magnets, protein tags, any antibody epitope, any specific example of any of these; any combination between any of these, or any label now known or yet to be disclosed.

A label may be covalently attached to a biomolecule or bound through hydrogen bonding, Van Der Waals or other forces. A label may be covalently or otherwise bound to the N-terminus, the C-terminus or any amino acid of a polypeptide or the 5' end, the 3' end or any nucleic acid residue in the case of a polynucleotide.

One particular example of a label is a protein tag. A protein tag comprises a sequence of one or more amino acids that may be used as a label as discussed above, particularly for use in protein purification or as a fluorescent label. In some examples, the protein tag is covalently bound to the polypeptide. It may be covalently bound to the N-terminal amino acid of a polypeptide, the C-terminal amino acid of a polypeptide or any other amino acid of the polypeptide. Often, the protein tag is encoded by a polynucleotide sequence that is immediately 5' of a nucleic acid sequence coding for the polypeptide such that the protein tag is in the same reading frame as the nucleic acid sequence encoding the polypeptide. Protein tags may be used for all of the same purposes as labels listed above and are well known in the art. Examples of protein tags include chitin binding protein (CBP), maltose binding protein (MBP), glutathione-S-transferase (GST), poly-histidine (His), thioredoxin (TRX), FLAG®, V5, c-Myc, HA-tag, green fluorescent protein (GFP) modified GFPs and GFP derivatives and other fluorescent proteins, such as EGFP, EBFP, YFP, BFP, CFP, ECFP and so forth. A His-tag which facilitates purification and binding to on metal matrices, including nickel matrices, including nickel matrices bound to solid substrates such as agarose plates or beads, glass plates or beads, or polystyrene or other plastic plates or beads. Other protein tags include BCCP, calmodulin, Nus, Thioredoxin, Strep, SBP, and Ty, or any other combination of one or more amino acids that can work as a label described above. Other examples of labels include a FRET donor, such as cyan fluorescent protein (CFP), a FRET acceptor such as 7-nitrobenz-2-oxa-1,3-diazolyl.

Mutation: A mutation may refer to any difference in the sequence of a biomolecule relative to a reference or consensus sequence of that biomolecule. A mutation may be observed in a nucleic acid sequence or a protein sequence. Such a reference or consensus sequence may be referred to as "wild type". A mutation in a protein relative to a wild type may result in a reduction in function of the expressed protein, a gain in function of the expressed protein, no change in function of the protein, a change in protein folding such as higher or lower efficiency of folding, a disease such as cystic fibrosis, a selective advantage, a selective disadvantage, or any other molecular, cellular, or organismal, effect.

A mutation may comprise any of a number of changes alone or in combination. Some types of mutations include point mutations (involving single amino acids); deletions (differences in which one or more amino acids are missing); or any other difference in protein sequence between one or more individuals or one or more cells within an individual (e.g. in mosaicism). A mutation that results in a difference in one or more amino acids may also be called an amino acid substitution mutation.

In some examples of the disclosed method, the mutation is a three base deletion in the nucleotide coding sequence for NBD1 domain of the CFTR polypeptide that results in an amino acid deletion that renders the polypeptide incapable of folding correctly, such as a deletion of the phenylalanine (F) at position 508 of the wild type CFTR.

Operably Linked: A first nucleic acid sequence is operably linked with a second nucleic acid sequence when the first nucleic acid sequence is placed in such a way that it has an effect upon the second nucleic acid sequence. For instance, a promoter is operably linked to a coding sequence if the promoter affects the transcription or expression of the coding sequence. Operably linked DNA sequences may be contiguous, or they may operate at a distance.

Promoter: A promoter may be any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of skill in the art. A nucleic acid comprising a promoter operably linked to a nucleic acid sequence that codes for a particular polypeptide can be termed an expression vector.

Purification: Purification of a complex may be achieved by any method now known or yet to be disclosed. In some examples, purification is achieved by contacting the complex with a reagent that binds to a component of the complex to the exclusion of other components. One example of a purification method is size exclusion chromatography.

Sequence homology: Sequence homology between two or more nucleic acid sequences or two or more amino acid sequences, may be expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75). For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). In addition, a manual alignment can be performed. Proteins with even greater similarity will show increasing percentage identities when assessed by this method, such as at least about 50%, 60%, 70%, 75%, 80%, 85%, 90%, 95%, 98%, 99%, or 100% sequence identity.

When aligning short peptides (fewer than around 30 amino acids), the alignment is to be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 50%, 60%, 70%, 75%, 80%, 85%, 90%, 95%, 98%, or 99% sequence identity to a protein. When less than the entire sequence is being compared for sequence identity, including a comparison of a dominant negative GW182 polypeptide, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

A pair of proteins or nucleic acids with 50%, 60%, 70%, 75%, 80%, 85%, 90%, 95%, 98%, or 99% identity to one another can be termed 'homologs,' particularly if they perform the same function as one another, even more particularly if they perform the same function to substantially the same degree, and still more particularly if they perform the same function substantially equivalently. One of skill in the art in light of this disclosure, particularly in light of the Examples below, would be able to determine without undue experimentation whether or not a given protein or nucleic acid sequence with 50%, 60%, 70%, 75%, 80%, 85%, 90%, 95%, 98%, or 99% identity to the sequences listed herein is a homolog to the sequences listed herein. Homologs need not be the same length as the biological molecules listed herein and may include truncations (fewer amino acids or nucleotides) or extensions (more amino acids or nucleotides) than the biological molecules listed herein.

Solid Support: Well-known solid supports or carriers include glass, silicone dioxide or other silanes, polyvinyl, polystyrene, polypropylene, polyethylene, dextran, nylon, amylases, natural and modified celluloses, polyacrylamides, hydrogels, gold, platinum, microbeads including agarose microbeads, micelles and other lipid formations, and magnetite. The affinity binding reagent may be affixed, bound (covalently or otherwise) attached, or printed onto a solid support either singly or with a plurality of similar or different biomolecules in the format of an array.

Specific Binding Reagent: A reagent capable of specific binding to a biomolecule may be any reagent that associates preferably (in whole or in part) with a particular biomolecule. A reagent binds specifically when it binds predominantly to a ligand. It is recognized that a minor degree of non-specific interaction may occur between a molecule, such as a specific binding reagent and an off-target biomolecule. Nevertheless, specific binding can be distinguished as mediated through specific recognition of the biomolecule by the reagent.

Specific binding reagents typically bind to a ligand with a more than 2-fold, such as more than 5-fold, more than 10-fold, more than 100-fold, or more than 10,000-fold greater amount of bound reagent (per unit time) to the ligand compared with the reagent's binding to a non-target (negative control) ligand. Specific binding may also be determined by a binding affinity calculation. Methods for performing such calculations are well known in the art. Specific binding results in binding affinity values calculated as [BR][L]/[BR·L] wherein BR=binding reagent and L=the ligand of the binding reagent on the order of $10^{-4}$, $10^{-5}$, $10^{-6}$, $10^{-7}$, $10^{-8}$, $10^{-9}$, $10^{-10}$ or lower. Examples of specific binding reagents include protein tags such as His or FLAG® tags, antibodies, natural ligands, engineered nanoparticles, or any other reagent capable of specific binding. An antibody may be any polypeptide that includes at least a light chain or heavy chain immunoglobulin variable region and specifically binds an epitope of an antigen. Antibodies can include monoclonal antibodies, polyclonal antibodies, or fragments of antibodies.

Test compound: A candidate molecule that promotes proper protein folding of a mutant protein that does not fold properly used in the disclosed methods. A test compound can include any small organic molecule, or a biological entity, for example a protein (such as an antibody or a peptide), a sugar, a nucleic acid (such as an antisense oligonucleotide, a ribozyme, or RNAi molecule) or a lipid. The test compound may be isolated, or may be part of a mixture (for example two or more test compounds). The test compound or mixture of test compounds may also include additional components, such as diluents, solvents, pharmaceutically acceptable carriers, or other compounds. In a particular example, a test compound is a pharmacoperone or other compound that can possibly alter protein folding.

DESCRIPTION

Figure 1:
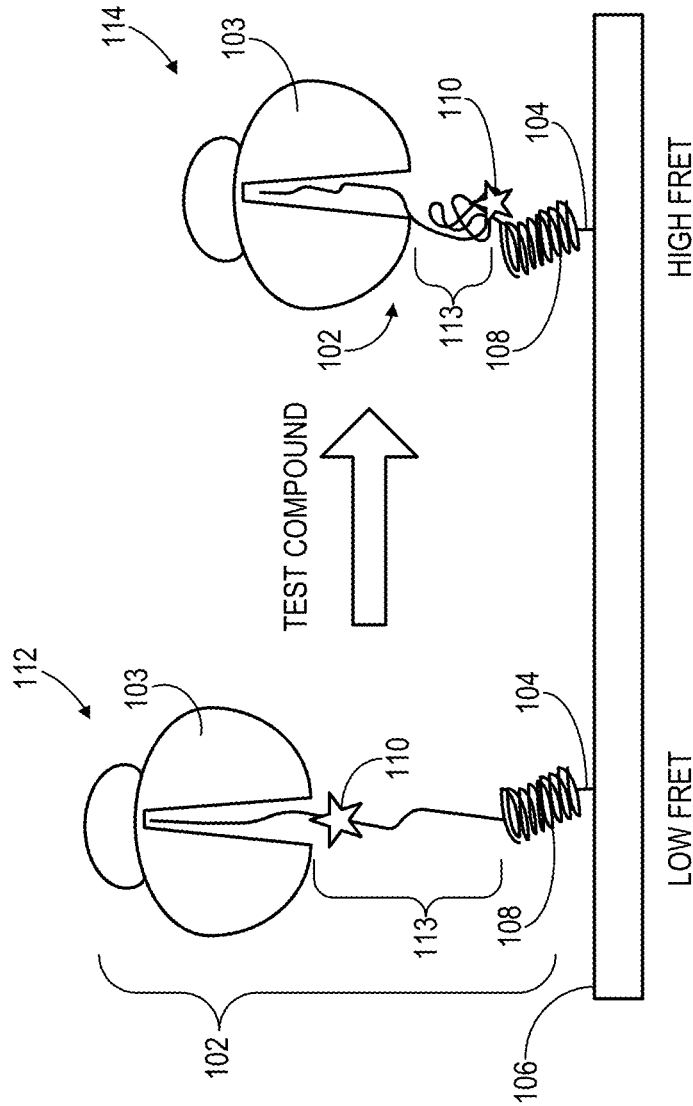
FIG. 1 illustrates a FRET analysis performed on a labeled ribosome-nascent-chain complex conjugated to a solid surface before and after treatment with a test compound.

The present disclosure is directed to methods and kits for monitoring protein folding directly on a ribosome using a solid-state system to immobilize tagged ribosome-nascent-chain complexes (RNCs) on a solid support. For example, as shown in the illustration of FIG. 1, a ribosome-nascent-chain complex 102 which includes a protein domain 113 bound to a ribosome 103 may include an attached protein tag 104 which is used to couple the ribosome-nascent-chain complex to a solid surface 106, e.g., an agarose bead or other suitable solid support. A FRET donor 108 and a FRET acceptor 110 may be incorporated into the ribosome-nascent-chain so that FRET images may be used to determine a folding state of the ribosome-nascent-chain complex under a variety of conditions.

For example, the ribosome-nascent-chain complex 102 shown in FIG. 1 may have a protein domain 113 which includes one or more mutations, e.g., the ΔF508 CFTR mutation described above, which reduces the folding efficiency of the ribosome-nascent-chain. Thus, as shown at 112 in FIG. 1, the immobilized ribosome-nascent-chain may be in a substantially unfolded position leading to a relatively low FRET efficiency. Test compounds may be applied to the immobilized ribosome-nascent-chain complex and FRET analysis may be performed to interrogate the effect of the test compound on the immobilized nascent peptide. For example, application of a test compound to the bound ribosome-nascent-chain shown in FIG. 1 may cause an increased amount of protein folding to occur as shown at 114. Thus, by coupling fluorescent-labeled ribosome-nascent-chain complexes to a solid support, rapid high throughput screens to identify small molecule compounds that alter protein structure and/or folding during cotranslational synthesis may be performed using FRET analysis. In particular, as remarked above, such an approach may be used to provide access to transient folding intermediates by the capture of the substrate at defined stages of the folding pathway to access ribosome-bound folding intermediates. Accessing ribosome-bound folding intermediates provides the potential to identify unique small molecules that act on the folding pathway and deter off-pathway reactions, in addition to those that stabilize the native folded state.

Figure 2:
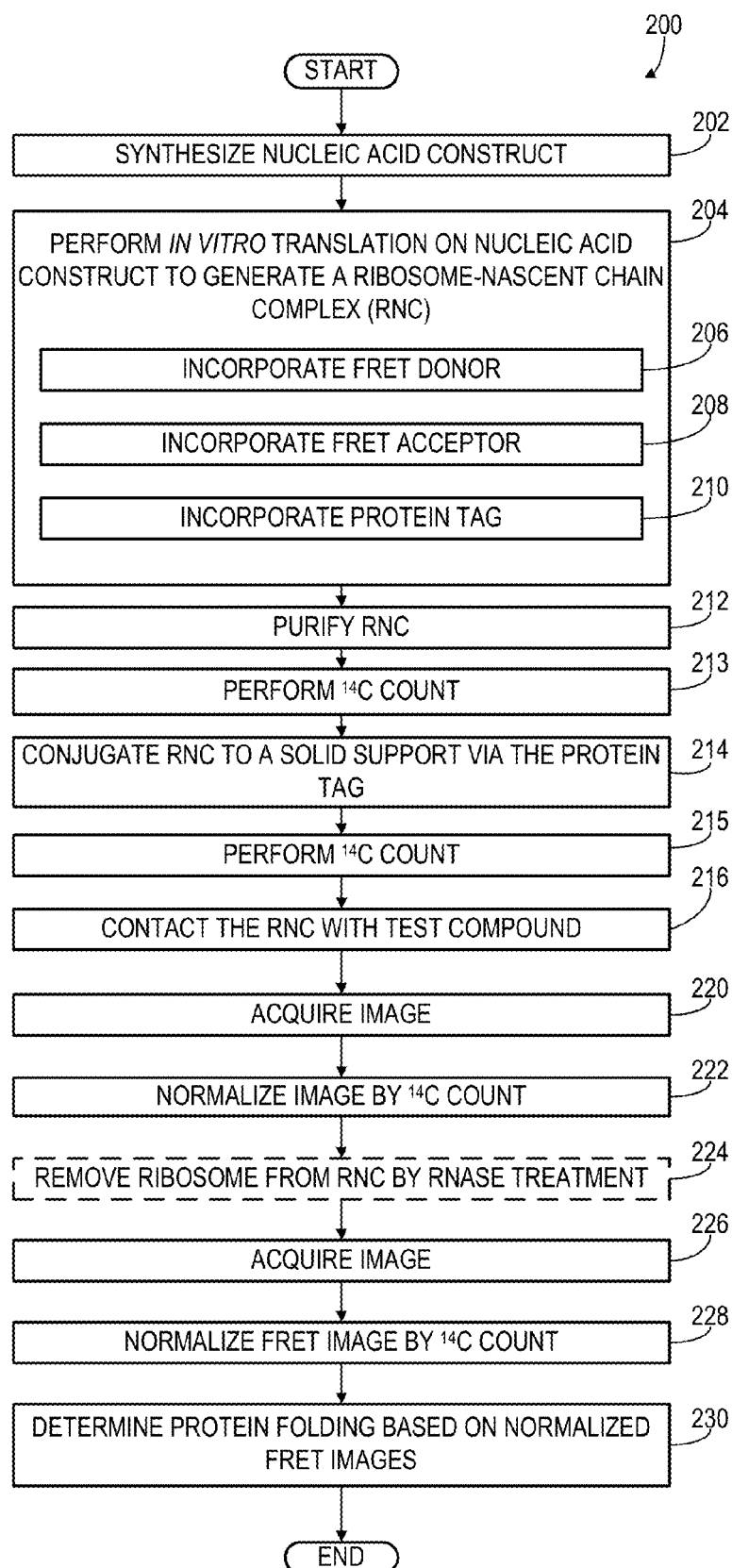
FIG. 2 shows an example method for detecting the folding of a protein domain in accordance with the disclosure.

Turning now to FIG. 2, FIG. 2 shows an example method 200 used in detecting folding of a protein domain by monitoring protein folding directly on a ribosome using a solid-state system to immobilize tagged ribosome-nascent-chain complexes (RNCs) on a solid support. As remarked above, by coupling fluorescent-labeled ribosome-nascent-chain complexes to a solid support, rapid high throughput screens to identify small molecule compounds that alter protein structure and/or folding during cotranslational synthesis may be performed using FRET analysis. In some examples, method 200 may be performed using components contained in a kit which includes suitable nucleic acid constructs, solid substrates, and reagents used to promote in vitro protein translation or monitor protein folding via FRET analysis. An example kit is described in more detail below.

At 202, method 200 includes synthesizing a nucleic acid construct to encode for an N-terminal tag used in affinity purification such as $His_{10}$ followed by a the coding sequence for a flexible linker to improve binding such as $(Ser-Gly-Gly)_7$ placed in frame with the coding sequence of a fluorescent protein such as cyan fluorescent protein (CFP) that is ligated to the coding sequence of the protein or protein domain of interest. For example a nucleic acid construct may be synthesized via a cloning strategy involving PCR amplification of specified DNA fragments and ligated into a suitable plasmid vector using standard tools of molecular biology. The synthesized nucleic construct may comprise a polynucleotide that encodes a protein domain, e.g., a protein domain derived from the first nucleic acid binding domain of CFTR, a polynucleotide that encodes a protein tag, e.g., a His-tag, and a polynucleotide that encodes a FRET donor, e.g., cyan fluorescent protein or enhanced cyan fluorescent protein.

In some examples, the protein domain may be a mutant protein domain, wherein the mutant protein domain is either unable to properly fold or folds into a structure with different characteristics or stability from the normal protein, thereby resulting in a FRET signal that differs from the that of the unmutated protein domain under certain physical conditions. For example, the mutant protein domain may be derived from the first nucleotide binding domain of CFTR and may include a $\Delta$F508 mutation.

At 204, method 200 includes performing in vitro translation on the nucleic acid construct to generate a ribosome-nascent chain complex (RNC). For example, in vitro translation may be carried out using any suitable reagent, e.g., rabbit reticulocyte lysate (RRL) as described in more detail below. During translation a FRET donor and/or a FRET acceptor may be incorporated into the RNC generated by the in vitro translation using the in vitro transcribed RNA template. For example, translation reactions may be performed to generate stable RNCS by eliminating the terminal stop codon in the coding sequence to prevent translation termination. Translations reactions may be programmed to produce RNCS containing one or more of a blank RNC with no Donor or Acceptor dye (B), RNCs with a Donor only (D), RNCs with an Acceptor only (A), and RNCs with a Donor+Acceptor (DA). For example, as described in Khushoo et al (2011) supra four reactions were translated in parallel in the presence of 0.8-1 $\mu$M $[^{14}C]$Lys-tRNAamb or $\epsilon$-NBD-$[^{14}C]$Lys-tRNAamb to generate samples containing: Blank with no Donor or Acceptor dye (B), Donor only (D), Acceptor only (A), and Donor+Acceptor (DA).

Thus, at 206, method 200 may include incorporating a FRET donor into the nascent protein during in vitro translation. For example, as described in more detail below, a donor fluorophore, such as cyan fluorescent protein (CFP), may be incorporated during translation via an in-frame N-terminal fusion of its coding sequence with that of the protein domain of interest such that it forms the N-terminal domain of the in vitro translated polypeptide. At 208, method 200 may include incorporating a FRET acceptor into the nascent protein during an in vitro translation. For example, as described in more detail below, a small acceptor dye such as 7-nitrobenz-2-oxa-1,3-diazole (NBD) may be incorporated at an engineered 'UAG' stop codon using a synthetic amber suppressor tRNA, $\epsilon$NBD-[14C]LystRNAamb during translation This suppressor tRNA is either synthesized in vitro or purified from cells. It may then be charged with an amino acid such as lysine or cysteine, which is then chemically modified with a small molecule that exhibits appropriate spectroscopic properties to absorb energy from the excited donor fluorophore such as CFP. The acceptor can be incorporated into the protein domain of interest as the protein is synthesized by the ribosome by cognate base pairing between the suppressor tRNA anticodon (CUA) and the stop codon (UAG) that is engineered into the protein coding sequence inserted into the polynucleotide vector. Further, the RNC may be labeled with $^{14}C$, e.g., via incorporation of the FRET acceptor using tRNA, $\epsilon$NBD-[14C]LystRNAamb in which the charged amino acid contains a radioisotope such as [14C] that can be used to detect and quantitate the amount and concentration of the translation product. In some examples, the FRET acceptor may be incorporated at a position along the nascent polypeptide and relative to the FRET donor so that FRET efficiency will either be constant (such as residue Thr389) or will depend upon the folded state or stability of the protein of interest (such as residue R450).

Further, at 210, method 200 may include incorporating a protein tag, e.g., a His-tag, during translation. For example, a poly-histidine tag may be added at the N-terminus by the translating ribosome when it is preceded by an AUG translation start codon. In some examples, at 212, method 200 may include purifying the RNC. For example, size exclusion chromatography may be used to purify the RNC following translation to remove free nascent polypeptides that either lack the acceptor dye (e.g. failed to read through the UAG stop codon) or detached prematurely from the ribosome. If an N-terminal peptide tag is used, such as the His-tag, this would alter stoichiometry of donor and acceptor and prevent accurate measurements of FRET.

At 213, method 200 may include performing a [$^{14}$C] count. For example, if each RNC is labeled with $^{14}$C, then the $^{14}$C count may correspond to the number of RNCs present. Any suitable isotopic label measurement technique may be used to perform a $^{14}$C count, e.g. mass spectrometry or liquid scintillation counting of samples.

At 214, method 200 includes conjugating the RNC to a solid support via the protein tag. For example, the solid support may comprise a nickel matrix, such as with a Ni-agarose bead or other optically neutral surface to which the RNC is conjugated following translation that allows accurate quantification of donor fluorescence. In some examples, the RNC may be conjugated to the solid support at a predetermined density needed to optimize fluorescence imaging and maximize signal to noise to improve reproducibility. This density is determined based on RNC concentration (measured by isotope counting) in which donor and donor plus acceptor samples are adjusted to equivalent concentrations prior to immobilization on solid support. For example, the ribosome-nascent chain complex may be conjugated to the solid support at a density of at least 800 complexes per square micron, which is close to the theoretical maximum.

At 216, method 200 may include contacting the RNC with a test compound. For example, the ribosome-nascent chain complex comprising a mutant protein domain may be contacted with a test compound so that the effect of the test compound on the folding behavior of the RNC can be assessed.

At 218, method 200 may include determining the stoichiometry of Donor and Donor plus Acceptor RNCs that are bound to their respective beads and confirm that they are bound in equal densities by $^{14}$C count. For example, if each RNC is labeled with $^{14}$C, then the $^{14}$C count may correspond to the number of RNCs present. Any suitable isotopic label measurement technique may be used to perform a $^{14}$C count, e.g. mass spectrometry, nuclear magnetic resonance, use of a scintillation counter, exposure to photographic film, or any other method of measuring radioactive isotopes.

At 220, method 200 includes using fluorescence microscopy to image beads containing RNCS. For example, a fluorescence signal may be detected at the emission wavelength of the FRET donor within the RNC. At 222, method 200 may include normalizing the FRET image by the $^{14}$C count obtained at step 218. In some examples, at 224, method 200 may include removing the ribosome from the RNC by RNAse treatment to detect folding that occurs as the nascent polypeptide emerges from the ribosome. At 226, method 200 may include reimaging the CFP-labeled support after the ribosome is removed; and at 228, method 200 may include normalizing this FRET image by the $^{14}$C count to allow comparison of FRET for polypeptides that remain attached to the ribosome and after their release.

At 230, method 200 includes interpretation of protein folding based on the normalized image intensities and calculated FRET. For example, a FRET value that is lower than the fluorescence signal of a protein domain with the donor alone may indicate the degree of proximity between donor and acceptor probes which may decrease, during folding of the protein domain. In the example where the protein domain is a mutant protein domain that is unable to properly fold, the resulting fluorescence signal may be greater than that of the unmutated protein domain. As another example, if contacting a nascent polypeptide with a mutant protein domain with a test compound results in a fluorescent signal that is less than that of the mutant protein domain without the test compound, then the test compound may be identified as promoting proper protein folding.

As remarked above, such an approach may be used to perform rapid high throughput screen by automated image capture and morphometric image analysis software to quantify CFP emission intensity per molecule of RNC bound. Screening a chemical library of small molecules may thereby identify small molecule compounds that alter protein structure and/or folding during cotranslational synthesis. Alternatively, such an approach may be used to determine whether or not a mutation in an amino acid results in altered folding of the domain. By coupling the protein to a solid support, FRET sensitivity is increased when compared to standard solution based measurements. For example, results demonstrated that as little as approximately 5 attomole ($5 \times 10^{-18}$ mole or approximately 3 million molecules) of in vitro synthesized, nascent NBD1 can be readily detected by fluorescence microscopy when immobilized at surface densities that approach 1000 RNCs/$\mu m^2$ using beads of suitable size. At current capture efficiencies (60% of purified RNCS), a standard 250 µl translation reaction therefore yields sufficient material for a minimum of 200,000 separate fluorescent measurements when incubated with appropriate beads and optimal times and RNC concentrations. This represents a $10^5$ fold improvement in sensitivity over conventional solution based FRET studies using the most sensitive instruments to detect in vitro synthesized RNC products. To determine whether substrate immobilization affected NBD1 folding, FRET was measured on matched beads containing either Donor or Donor+Acceptor probes. As a control, isotopic incorporation of the FRET Acceptor dye at residue 389 in NBD1 (residue 1 in SEQ ID NO: 2) yielded 61-67% FRET that was independent of nascent protein length as predicted, in excellent agreement with solution-based studies. Placing the acceptor dye at residue 450 (residue 67 of SEQ ID NO: 2) further showed that immobilized NBD1 undergoes N-terminus subdomain folding as residues 500-550 move outside the ribosome tunnel, and that kinetically trapped unfolded NBD1 (with a truncation at residue 500) can be folded on the bead upon ribosome release. Thus, solid state measurements recapitulate nascent polypeptide folding observed in solution and define a versatile, high throughput system for interrogating structural changes in nascent polypeptide folding intermediates by high throughput microscopy. As such, it provides a promising CF drug discovery platform for screening small molecule compounds that interact with and stabilize nascent NBD1, for example.

Solid state FRET can also discriminate maneuvers that positively and negatively impact folding. For example, NBD1 unfolding may be accomplished using denaturants such as urea. Alternatively, the N-terminal subdomain may be converted to a less folded state through induced chemical shift by addition of a monoclonal antibody that binds to the intrinsically unstructured regulatory insertion. Induced folding may be detected in a similar manner by increased FRET such can be observed following deletion of the regulatory insertion peptide.

Disclosed herein are kits that facilitate the performance of the disclosed methods. For example, method 200 described above may be performed using components contained in a kit which includes suitable nucleic acid constructs, solid substrates, and reagents used to monitor protein folding via FRET analysis. An example kit is described in more detail below. A schematic diagram of an example kit 2000 is shown in FIG. 20.

A kit is an assemblage of components that may be used in the performance of the method. Use of kits provides advantages to the end user of the method in that the components may have been standardized, the components may have been subject to quality assurance, the components may have been subject to sterilization, or the proportions and characteristics of the various components may have been optimized for maximal efficacy. In addition, a kit may provide the advantage that the components of the kit are obtained from a single source. This in turn makes preparations for the performance of the method as well as troubleshooting problems with the method more efficient. Components may be enclosed in one or more containers appropriate for their storage, such as vials, tubes, bottles, or any other appropriate container. The containers may be further packaged into secondary containers such as boxes, bags, or any other enclosure.

Figure 12:
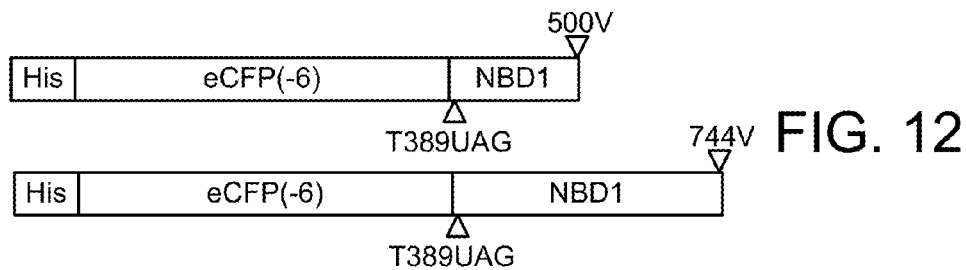
FIG. 12 schematically shows a CFP-NBD1 nascent polypeptide with an N-terminal His-tag and an acceptor probe site (UAG codon) at CFTR residue Thr389 and truncated at CFTR residues 550 and 744.

For example, kit 2000 shown in FIG. 12 may include a nucleic acid construct 2002 that encodes a ribosome-nascent chain complex during in vitro translation, wherein the construct comprises a polynucleotide that encodes the protein domain, a polynucleotide that encodes a protein tag, and a polynucleotide that encodes a FRET donor. Kit 2000 may also include a solid substrate 2004, e.g., agarose beads or some other suitable support. Kit 2000 also includes one or more reagents 2006 capable of carrying out in vitro translation on the nucleic acid construct to thereby generate a ribosome-nascent chain complex comprising the protein domain, the protein tag, the FRET donor, and a FRET acceptor. The reagents may further be capable of binding the ribosome-nascent chain complex to a solid substrate via the tag. Such a kit may contain a plasmid cloning vector containing the His-tag in frame with CFP coding sequence and suitable restriction sites for inserting the domain of interest. Included would be aliquots of two matched suppressor tRNAs, one with an acceptor probe attached and the other lacking the probe to be used as a control, e.g. εNBD-Lys-tRNA$^{amb}$ and Lys-tRNA$^{amb}$, respectively. The kit may also contain an aliquot of purified RNA aptamer, which inhibits eukaryotic termination factors. The function of aptamer is to enhance stop codon readthrough and improve incorporation efficiency of probes, and hence yield of usable RNCs. The kit may also contain premixed aliquots of translation mixtures or components of translation mixtures that are suitable for performing in vitro translation of synthetic RNA transcripts, e.g. reticulocyte lysate. The kit may include a reagent capable of purifying RNCS and solid support for binding RNCS prior to microscopic imaging.

A kit may further comprise instructions 2008 describing how to perform the method. The instructions may be any description of the method that is provided with, referred to by, or otherwise indicated by a component of the kit. The instructions may be communicated through any tangible medium of expression. The instructions may be printed on the package material, printed on a separate piece of paper or any other substrate and provided with or separately from the kit. They may be printed in any language and may be provided in picture form. The instructions may be posted on the internet, written into a software package, or provided verbally through a telephone or by an email conversation or provided as a smart phone application. The instructions may be said to describe how to perform the method if the instructions provide a recipe of how to perform the method, if they refer a user to a publication wherein a description of the method may be found, or in any other way inform any end user of how to perform a method of detecting the folding of a protein domain in accordance with the disclosed methods.

It will be appreciated that the materials, compositions, configurations, and routines disclosed herein are exemplary in nature, and that these specific embodiments are not to be considered in a limiting sense, because numerous variations are possible. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

EXAMPLES

The following examples are illustrative of disclosed methods. In light of this disclosure, those of skill in the art will recognize that variations of these examples and other examples of the disclosed method would be possible without undue experimentation.

Example 1

FRET System

Advantages to the use of FRET: Use of a FRET system to analyze folding off of a ribosomal RNA provides a rigorous and quantitative system that further allows the interrogation of co-translational folding. The assay proceeds quickly, with translation of DNA to protein complete in about 3 hours. No large scale purification is necessary. Challenges are that 4 translations are necessary (at 250 µL each). Proteins are produced at a low concentration (at about 1-5 nM) and in limited quantity (in a range of 250-1000 femtomoles of protein.) Finally, use of FRET on a solid surface requires a precise stoichiometry of ribosome-nascent chain complexes on the surface.

In general, ribosome-nascent chain complexes are immobilized at a surface area at about 1000 molecules per square micrometer. Fluorescence microscopy is used to detect the FRET. FRET may be measured by any of a number of methods including D/DA ratio and acceptor photobleaching. FIG. 1 described above illustrates a FRET analysis performed on a labeled ribosome-nascent-chain complex conjugated to a solid surface before and after treatment with a test compound.

Example 2

Methods

Figure 4:
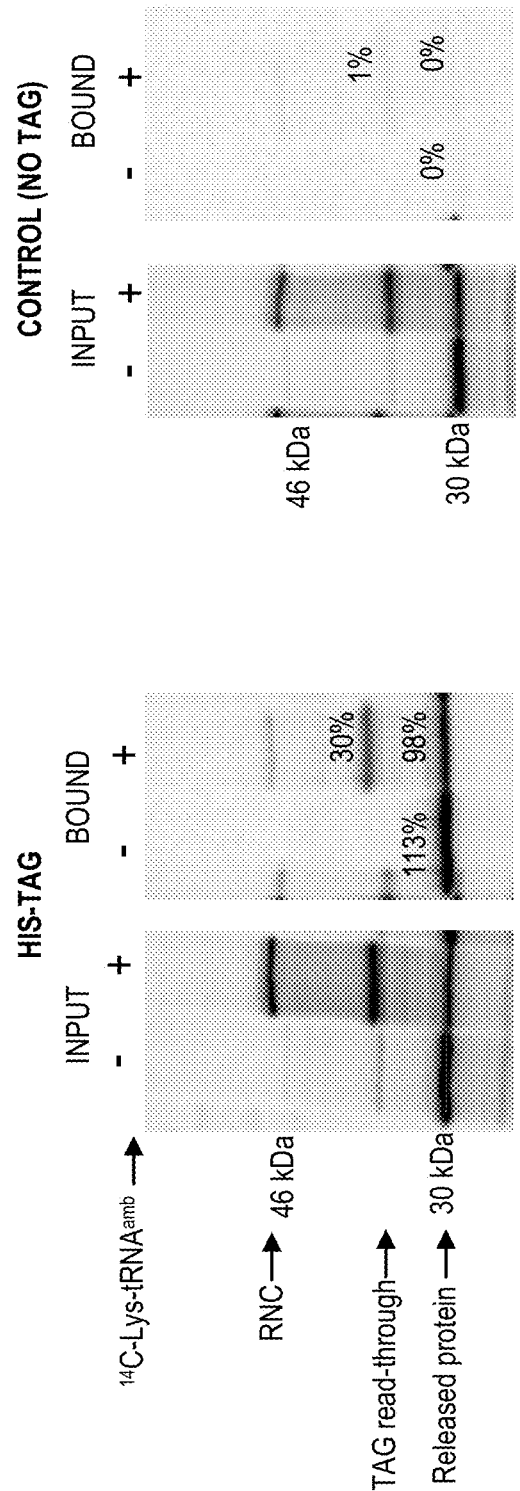
FIG. 4 shows an autoradiogram demonstrating a bead binding efficiency of the ribosome-bound nascent polypeptide shown in FIG. 3.

In vitro translation of His-eCFP-NDB1 constructs for SDS-PAGE analysis were performed by the following method: translation is performed in a solution comprising 1 µl of RRL (rabbit reticulocyte lysate) translation solution, 1000 Ni-NTA agarose beads, 500 µl of a buffer comprising 20 mM imidazole, 40 mM HEPES pH 7.6 and 100 mM KOAc, 15 mM Mg(OAc)$_2$, 0.1 mM DTT. The solution is rotated for 2 hours at room temperature and centrifuged for 3 minutes at 500×g at 4° C. The buffer is then removed and the beads are then washed twice with 500 µl of clean buffer of the same composition. The beads are then analyzed by high content microscopy. Bound His-eCFP-NDB1 is eluted by the addition of 0.5M imidizole buffer. Then SDS-PAGE sample buffer is added to the eluate and the eluate is further analyzed on an SDS-PAGE gel. FIG. 3 schematically shows a ribosome-bound CFP-NBD1 nascent polypeptide with an N-terminal His-tag and an acceptor probe incorporated at Thr389 and truncated at CFTR residue 445. The RNC shown in FIG. 3 is called His-eCFP(-6)-NBD1 T389TAG ↓445V. An example of a gel from the in vitro translation of the construct called His-eCFP(-6)-NBD1 T389TAG ↓445V is shown in FIG. 4. In particular, FIG. 4 shows an autoradiogram demonstrating a bead binding efficiency of the ribosome-bound nascent polypeptide shown in FIG. 3.

Figure 6:
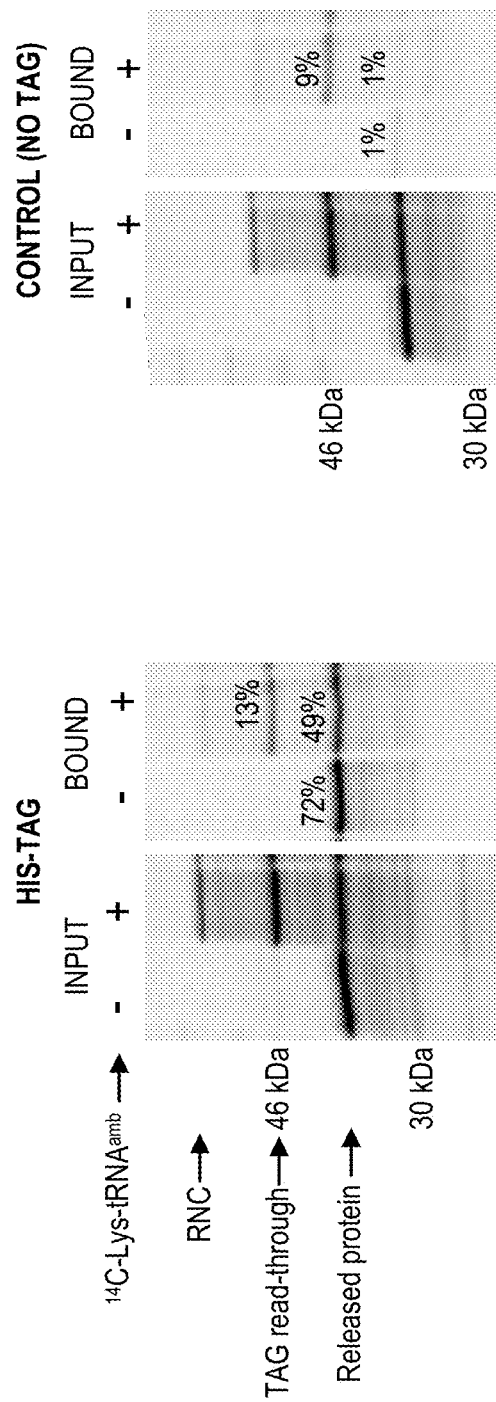
FIG. 6 shows an autoradiogram demonstrating a bead binding efficiency of the ribosome-bound nascent polypeptide shown in FIG. 5.

FIG. 5 schematically shows a ribosome-bound CFP-NBD1 nascent polypeptide with an N-terminal His-tag and an acceptor probe incorporated at Arg450 and truncated at CFTR residue 550. The RNC shown in FIG. 5 is called His-eCFP(-6)-NBD1 R450TAG ↓550V and an example of a gel from the in vitro translation of the construct called His-eCFP(-6)-NBD1 R450TAG ↓550V is shown in FIG. 6. In particular, FIG. 6 shows an autoradiogram demonstrating a bead binding efficiency of the ribosome-bound nascent polypeptide shown in FIG. 5. Bead binding affinity is calculated by the formula: Bead binding efficiency=Bound/Input.

In vitro translation of His-eCFP-NBD1 constructs for use in analysis of protein folding by FRET was performed by the following method: ribosome-nascent chain (RNC) complexes are purified from a 250 µl volume of the in vitro translation solution prepared as described above by size-exclusion chromatography. The purified RNC are then bound to Ni-NTA agarose beads as follows: purified RNC at 3 nM are combined with 5000 Ni-NTA agarose beads and a buffer comprising 20 mM imidazole, 40 mM HEPES pH 7.6, 100 mM KOAc, 15 mM Mg(OAc)$_2$, and 0.1 mM DTT in a total volume of 600 µl. The beads are rotated at room temperature, centrifuged and pelleted, and washed twice in the same buffer. $^{14}$C labeled proteins are used in analyses of binding efficiency. $^{14}$C counts are counted in a sample to determine efficiency of binding of the RNC to the beads. FRET imaging is then performed before and after the addition of 3 mM ATP and treatment with RNAse. $E_{FRET}$ is determined by the formula $E_{FRET}$=1−DA/D. $^{14}$C corrected CFP emission is determined by the formula CFP emission/µM$^2$/Number of proteins/µM$^2$=CFP emission/molecule.

Example 3

His-eCFP-NBD1 Capture on Ni-NTA Beads

SDS-PAGE analysis of His-eCFP-NBD1 bead binding is described in Example 2 above. 1 µl of RRL translation solution was combined with 100 Ni beads. A His-eCFP(-6)-NBD1 T389TAG truncated at 445V construct is illustrated in FIG. 3. The efficiency of the construct in binding to Ni beads is illustrated in the SDS PAGE gel of FIG. 4. The His-tagged construct binds the beads with far greater efficiency (FIG. 4, left panels) than the construct lacking the His-tag. A His-eCFP(-6)-NBD1 R450TAG truncated at 550V construct is illustrated in FIG. 5. The efficiency of this construct in binding to Ni beads is illustrated in the SDS-PAGE gel of FIG. 6. The His-tagged construct binds the beads with far greater efficiency than a construct lacking the His-tag. Bead binding efficiencies were calculated by the following formula [Bead binding efficiency=Bound/Input].

Example 4

Visualization of In Vitro Translated CFP-NBD1 Fragment

Figure 8:
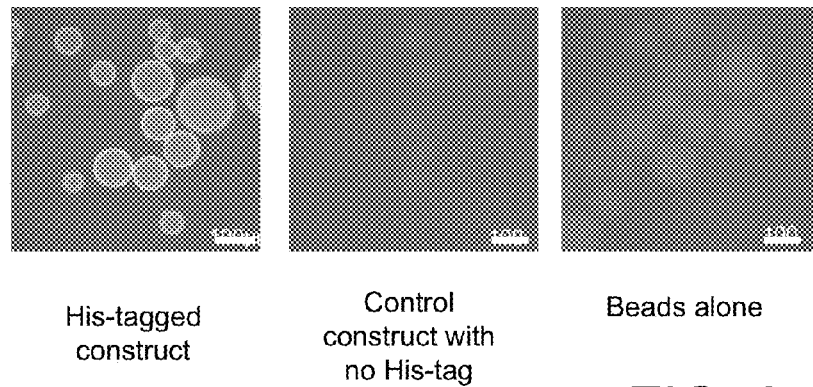
FIG. 8 shows example fluorescence micrographs of agarose bead-bound CFP-NBD1 nascent polypeptides with N-terminal His-tags truncated at CFTR residue 450, agarose beads incubated with polypeptides lacking the N-terminal His-tag, and empty agarose beads.
Figure 9:
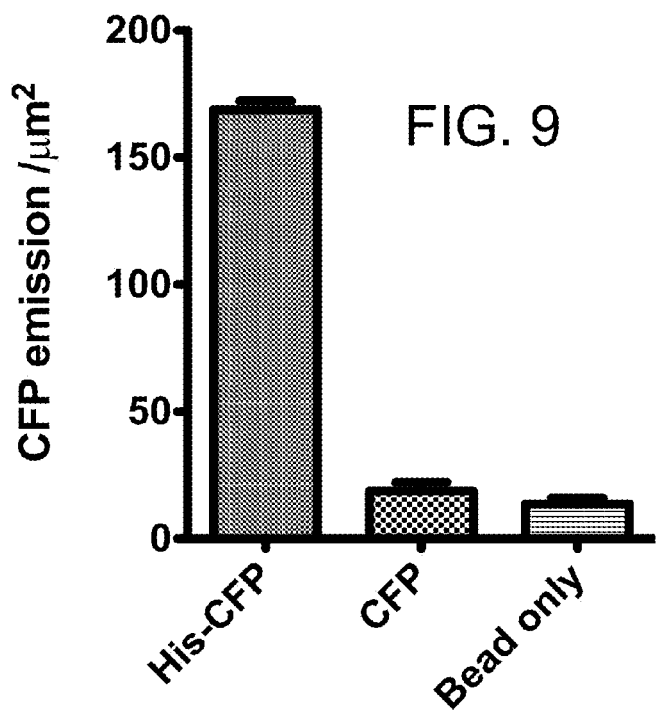
FIG. 9 shows a graph of quantification of CFP fluorescence intensity obtained by imaging Ni-NTA agarose beads containing bound His-tagged CFP-NBD1 polypeptides with N-terminal His-tags truncated at CFTR residue 450, and the same polypeptides without N-terminal His-tags, and a plot of background fluorescence intensity of empty agarose beads.

In vitro translation of RNC to Ni beads for FRET visualization was performed as described in Example 2 above. In particular, 1 µl of RRL translation solution was added with 1000 Ni beads. Binding efficiency was 70% with a total of 1×10$^{-17}$ moles of RNC per bead, which is about equivalent to 5×10$^6$ RNC molecules per bead. This results in a surface concentration of about 1000 molecules per square micron on the surface of the bead. Translation reactions were performed without $^{14}$C-Lys-tRNAamb. FIG. 7 schematically shows an in vitro synthesized ribosome-bound CFP-NBD1 nascent polypeptide with an N-terminal His-tag and an acceptor probe incorporated at Arg450. The construct shown in FIG. 7 is called His-eCFP(-6)-NBD1 R450TAG and is a representation of the construct used in this example. FIG. 8 shows a graph with a plot of CFP emission of agarose bead-bound and ribosome-bound CFP-NBD1 nascent polypeptides with N-terminal His-tags and acceptor probes incorporated at Arg450 and truncated at CFTR residue 450, a plot of CFP emission of agarose bead-bound and ribosome-bound CFP-NBD1 nascent polypeptides with acceptor probes incorporated at Arg450 but without N-terminal His-tags, and a plot of CFP emission of agarose beads. In particular, FIG. 8 is a bar graph showing the CFP emission/µm$^2$ of His-eCFP-NBD1 truncated at 450TAG, eCFP-NBD1 truncated at 450TAG without a His-tag (negative control), and unconjugated Ni-NTA agarose beads. Error bars indicate the emissions of 5-10 samples. CFP emission/µm$^2$ in FIG. 6 was calculated by the formula: CFP emission/µm$^2$=total CFP emission per area (in µM$^2$). FIG. 9 shows example CFP emission images of agarose bead-bound and ribosome-bound CFP-NBD1 nascent polypeptides with N-terminal His-tags and acceptor probes incorporated at Arg450 and truncated at CFTR residue 450, agarose bead-bound and ribosome-bound CFP-NBD1 nascent polypeptides with acceptor probes incorporated at Arg450 but without N-terminal His-tags, and agarose beads. In particular, FIG. 9 shows CFP emission images of His-eCFP-NBD1 truncated at 450TAG on beads (left panel), the same construct without the His tag incubated with beads (control), and Ni-NTA agarose beads. Scale bar, 100 µm. CFP emission of bead samples were observed at 37° C. using a high resolution widefield inverted microscope, (Olympus IX71) [Emission wave length, 470 nm (458-482 nm), excitation wavelength, 430 nm (418-442 nm)].

Example 5

Geometry of RNC Binding

A ribosome base has an effective cross sectional surface area of approximately 600 nm$^2$ per molecule. Therefore, the theoretical RNC density on a Ni-NTA agarose bead is 1600 molecules per square micron. The measured binding density of RNC on agarose beads is typically about 300-800 molecules per square micron but can approach and even potentially exceed theoretical saturation under optimal binding conditions.

Example 6

Capture Efficiency of eCFP-NBD1

FIG. 20 shows results when purified RNCs containing His-CFP-NBD1 with a [14C] probe at residue Arg450 and truncated at residue 550 were bound with various numbers of Ni-NTA agarose beads, various concentrations of RNCs, and various incubation times. Densities of His-eCFP-NBD1 on bead were calculated using number of total protein molecules in each bead binding samples from $^{14}$C count results and total surface area of beads. Results show excellent capture efficiencies of RNCS that exceed 70% binding efficiency, and achieve surface densities of greater than 500 RNCS per square micron.

FIG. 20 also shows a graph of CFP emission versus the number of agarose beads in one binding reaction with ribosome-bound CFP-NBD1 nascent polypeptides. In particular, the line graph shows the CFP emission/µm$^2$ for samples incubated with the indicated number of agarose beads in each reaction Panel F shows a graph of binding efficiency (binding/input) versus the number of agarose beads in one binding reaction with ribosome-bound CFP-NBD1 nascent polypeptides with N-terminal His-tags and [$^{14}$C] probes incorporated at Arg450 and truncated at CFTR residue 550. In particular, FIG. 12 is a line graph plotting the percentage of $^{14}$C labeled total protein bound to beads over the total amount of input protein against the number of beads in the reaction.

Example 7

FRET Detection Using Immobilized RNC's

FIG. 13 schematically shows a CFP-NBD1 nascent polypeptide with an N-terminal His-tag and an acceptor probe incorporation site at Thr389. In particular, FIG. 13 is a diagram showing the His-eCFP(-6)-NBD1 T389TAG construct truncated at either 500V or 744V (indicated by the arrows.) Translation reactions were performed with $^{14}$C-Lys-tRNA$^{amb}$ or NBD-$^{14}$C-Lys-tRNA$^{amb}$. Table 2 shows the densities of the indicated His-eCFP-NBD1 constructs on the beads.

TABLE 1

| Density of in vitro translated His-eCFP(-6)-NBD1 T389TAG on beads | |
|---|---|
| Construct | Protein density (proteins per µm$^2$) |
| ↓500 V Donor | 1397 |
| ↓500 V Donor-Acceptor | 1221 |
| ↓744 V Donor | 414 |
| ↓744 V Donor-Acceptor | 494 |

Figure 14:
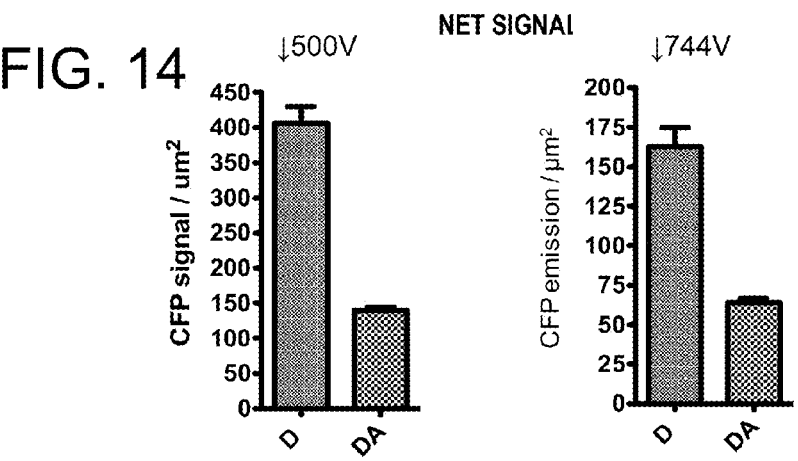
FIG. 14 shows a graph with plots of net CFP emission intensity obtained from agarose beads containing ribosome-bound NBD1 nascent polypeptides truncated at CFTR residues 500 and 744 with only the CFP donor incorporated and with both an N-terminal donor and an acceptor probe incorporated at Thr389 as shown in FIG. 13.
Figure 15:
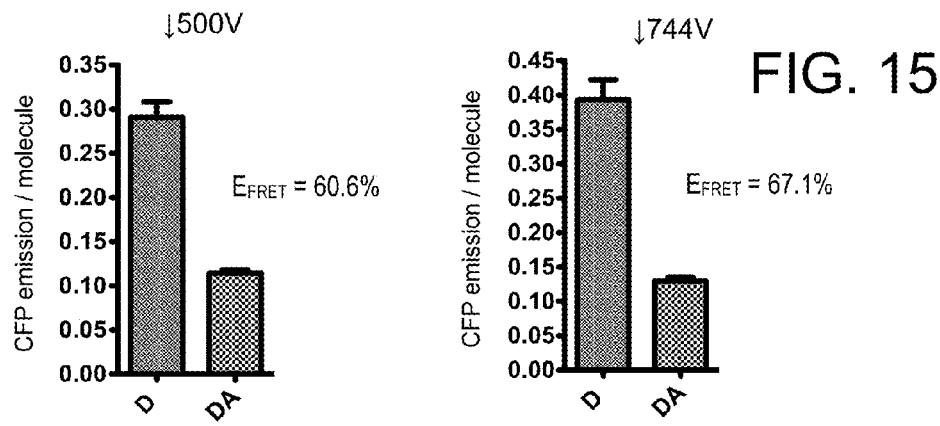
FIG. 15 shows a graph with plots of CFP emission intensity normalized by $^{14}C$ counts of agarose bead-bound and ribosome-bound NBD1 nascent polypeptides truncated at CFTR residues 500 and 744 with only the N-terminal CFP donor incorporated and with both the donor and an acceptor probe incorporated at Thr389.
Figure 16:
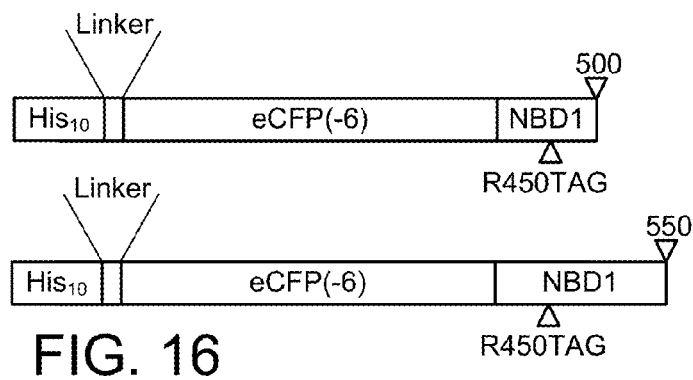
FIG. 16 schematically shows a CFP-NBD1 polypeptide with an N-terminal His-tag and an acceptor probe incorporation site at Arg450 and truncated at CFTR residues 500 and 550.

FIG. 14 shows example CFP emission images for agarose bead-bound and ribosome-bound NBD1 nascent polypeptides truncated at CFTR residues 500 and 744 with only the CFP donors incorporated and with both acceptor probes incorporated at Thr389 and CFP donors incorporated in the ribosome-bound NBD1 nascent polypeptides. In particular, FIG. 14 is an image showing CFP emission images: Left panels show Donor (CFP only) and right panels show Donor+ Acceptor (CFP plus NBD fluorescence dye). FIG. 15 shows a graph with plots of CFP emission of agarose bead-bound and ribosome-bound NBD1 nascent polypeptides truncated at CFTR residues 500 and 744 with only the CFP donors incorporated and with both acceptor probes incorporated at Thr389 and CFP donors incorporated in the ribosome-bound NBD1 nascent polypeptides. In particular, FIG. 15 shows the net signal CFP emission/µm$^2$ of samples bound to beads after subtracting the autofluorescence of Ni-NTA agarose beads. Error bars indicate SE of 5-10 samples. Left panels show the ↓500V construct, while right panels show the ↓744V construct. FIG. 16 shows a graph with plots of CFP emission normalized by $^{14}$C counts of agarose bead-bound and ribosome-bound NBD1 nascent polypeptides truncated at CFTR residues 500 and 744 with only the CFP donors incorporated and with both acceptor probes incorporated at Thr389 and CFP donors incorporated in the ribosome-bound NBD1 nascent polypeptides. In particular, FIG. 16 shows the CFP emission per molecule for the ↓500V construct and the ↓740V construct. FRET efficiencies were calculated by the formula $E_{FRET}=1-DA/D$, using $^{14}$C corrected data. CFP emission per molecule was calculated by the formula CFP emission per µm$^2$/number of proteins/µm$^2$.

Example 8

FRET Analysis of N-Terminal Subdomain Folding

FIG. 17 schematically shows a ribosome-bound CFP-NBD1 nascent polypeptide with an N-terminal His-tag and an acceptor probe incorporated at Arg450 and truncated at CFTR residues 500 and 550. In particular, FIG. 17 is a diagram of His-eCFP(-6)-NBD1 R450TAG truncated at 500V and 550V. Translation reactions were performed with 14C-Lys-tRNA$^{amb}$ or NBD-14C-Lys-tRNA$^{amb}$. Ribosomes were released from RNC on beads by RNase treatment.

Figure 18:
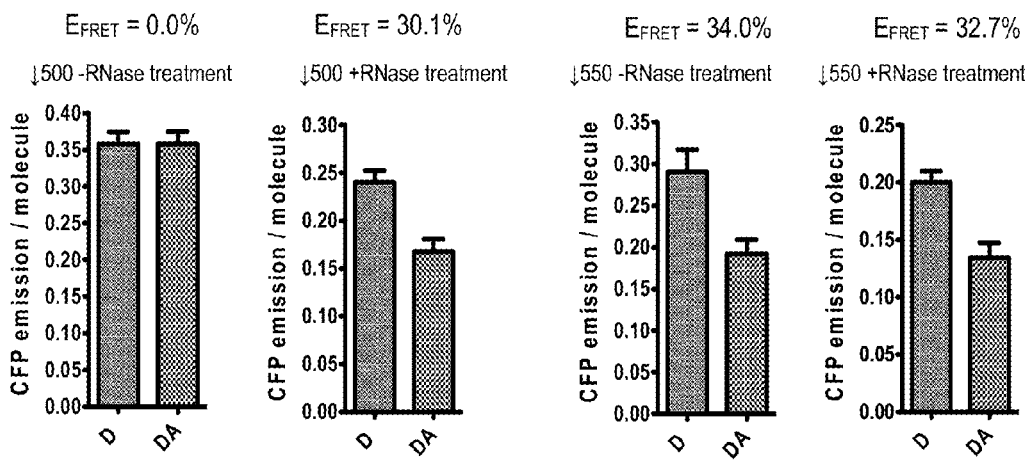
FIG. 18 shows graphs with plots of net CFP emission intensity normalized by $^{14}C$ counts of agarose bead-bound CFP-NBD1 nascent polypeptides with N-terminal His-tags and acceptor probes incorporated at Arg450 and truncated at CFTR residues 500 and 550 which are bound to ribosomes and released from ribosomes via treatment with RNase.
Figure 19:
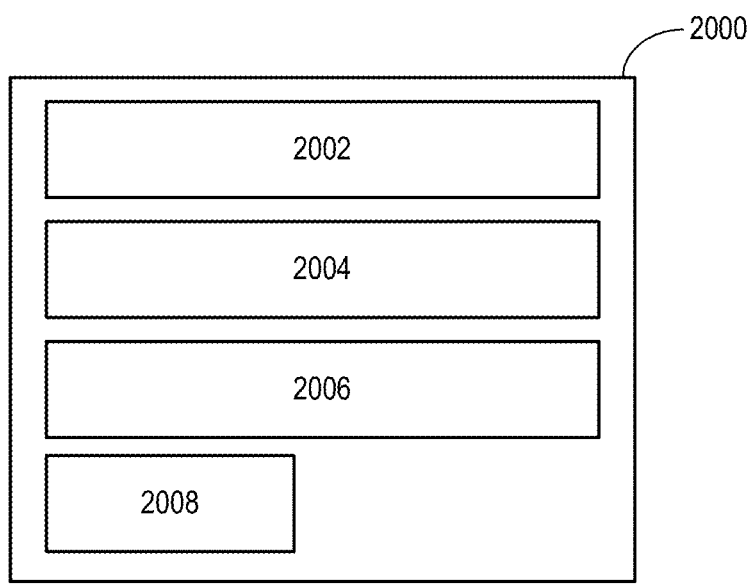
FIG. 19 shows a schematic diagram of an example kit for detecting the folding of a protein domain in accordance with the disclosure.
Figure 21:
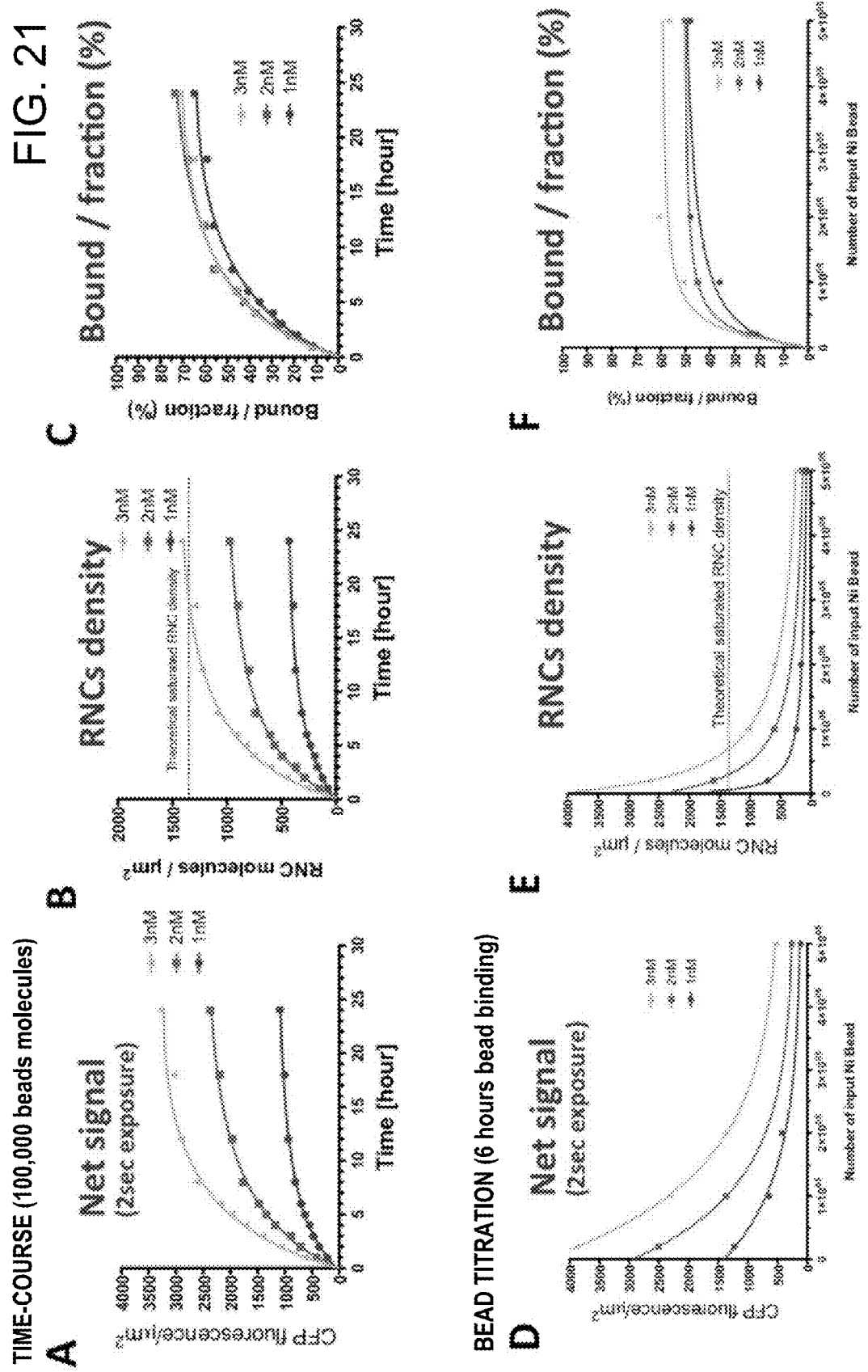
FIGS. 21A-21F show results of efforts to optimize yield of beads and ENC binding by varying RNC concentration in solution, binding time and bead number. Panels A, B and C show plots of CFP fluorescence intensity/$\mu m^2$, RNC density (determined by [14C] counting, and percent of total RNCs that are bound to beads as a function of incubation time, respectively, at three RNC concentrations. Panels D, E, and F show plots of CFP fluorescence intensity/$\mu m^2$, RNC density (determined by [14C] counting, and percent of total RNCs that are bound to beads as a function of number of beads in the binding reaction. Results show that acceptable fluorescent signal can be achieved for 200,000 beads using RNCS generated from a single 250 microliter translation reaction.
Figure 22:
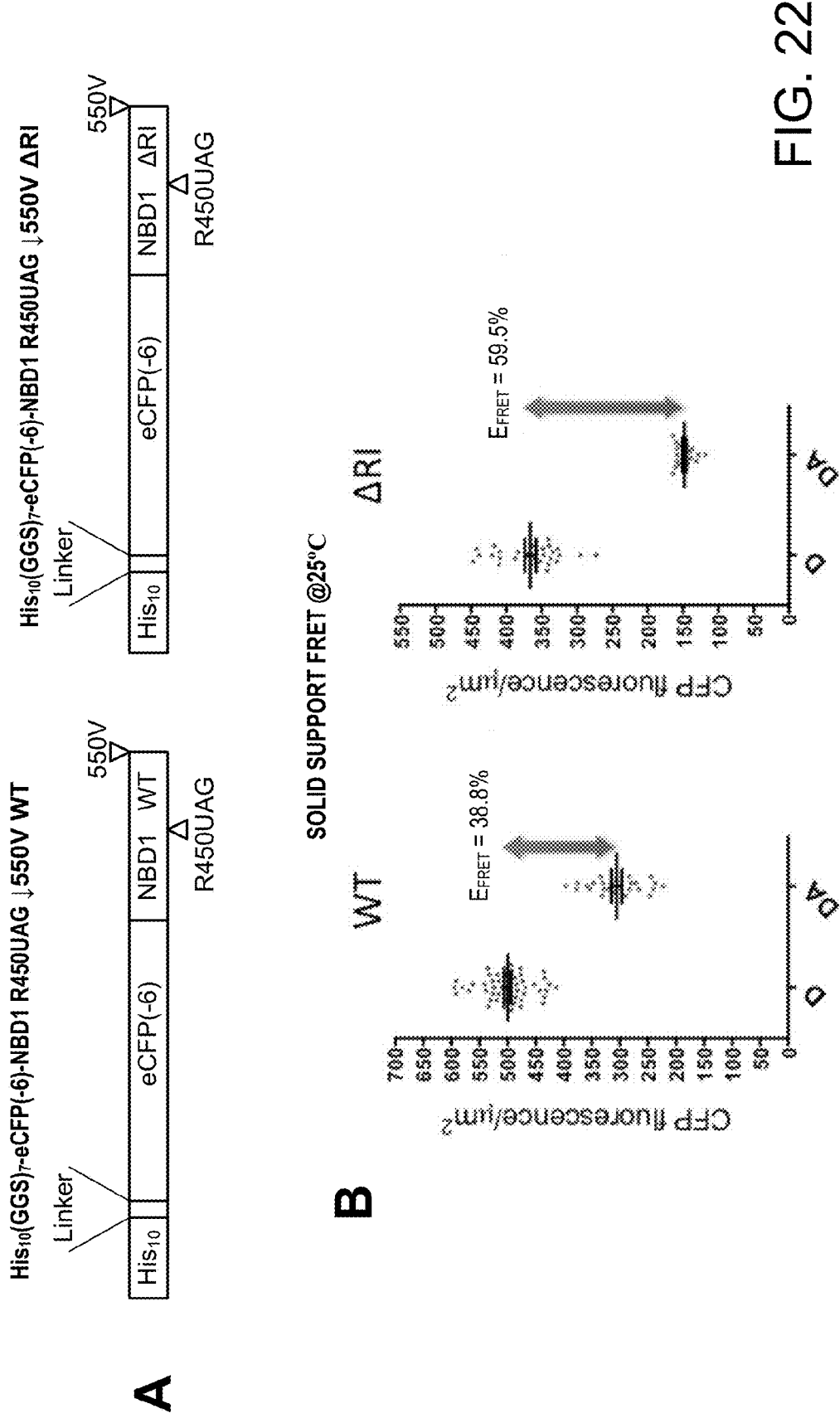
FIGS. 22A-22B show solid support FRET results obtained for His-tagged CFP-NBD1 containing the acceptor probe at residue Arg450 truncated at CFTR residue 550. Results show that folding of wild type NBD1 is improved following deletion of the unstructured regulatory insertion. This conclusion is supported by the increase in FRET from 39% (for wild type) and 60% (for the ΔRI construct). Thus, solid state FRET is able to detect different folding states of a nascent ribosome-bound polypeptide that are in good agreement with our solution-based FRET studies

FIG. 18 shows graphs with plots of CFP emission of agarose bead-bound CFP-NBD1 nascent polypeptides with N-terminal His-tags and acceptor probes incorporated at Arg450 and truncated at CFTR residues 500 and 550 which are bound to ribosomes and released from ribosomes via treatment with RNase. In particular, FIG. 18 is a set of bar graphs showing the net signal of CFP emission/µm$^2$ of samples after subtracting autofluorescence of Ni-NTA agarose beads. FIG. 19 shows graphs with plots of CFP emission normalized by $^{14}$C counts of agarose bead-bound CFP-NBD1 nascent polypeptides with N-terminal His-tags and acceptor probes incorporated at Arg450 and truncated at CFTR residues 500 and 550 which are bound to ribosomes and released from ribosomes via treatment with RNase. In particular, FIG. 19 shows the CFP emission/molecule ($^{14}$C corrected data). FRET efficiencies were calculated by the following formula, $E_{FRET}=1-DA/D$, using $^{14}$C corrected data. Ribosomes were released from RNC on beads by RNase treatment with 3 mM ATP.

Example 9

Automated Imaging of RNC Beads by High Content Microscopy and Image Analysis

FIG. 23 shows raw images of CFP-NBD1 immobilized on 34 micron agarose beads taken with the Nikon Ti-Eclipse microscope. The resulting pixel intensity histogram can be used to threshold the image to automatically select beads which can then be binned by size, circularity and other properties to improve statistical analysis. Average net fluorescence intensity of selected beads can then be used to compare a parallel RNC samples containing donor alone, and donor plus acceptor probes to determine FRET. For example, automated images readily distinguish wild type N-terminus subdomain folding (FRET=38%) from the more tightly folded domain that is lacking the regulatory insertion (ΔRI FRET=59%) in good agreement with solution based studies.

Example 10

Suitability of Solid State FRET Assay for High Throughput Screening in 384 Well Format FIG. 23 shows the analysis of wild type and RI deletion mutant for His-tagged CFP-NBD1 containing the acceptor probe at residue 450 and polypeptide truncated at residue 550. In this experiment, wild type and RI deletion mutant RNCs containing donor alone or donor plus acceptor were bound to 34 micron beads and plated in two sets of twelve rows each. Images were captured and average net fluorescent signals from beads were analyzed as described in example 9 and plotted in the top graph. This data was analyzed as described in Example 9 to generate 24 replicate FRET measurements each for wild type and RI deletion mutant. Statistical analysis of FRET values revealed a wild type FRET of 44.3% with a standard deviation of 1.6 for wild type and 61% with a standard deviation of 1.3% for the RI deletion mutant. This gives a coefficient of variance of 3.6% and 2.2% respectively and a Z factor of 0.5 which is predictive of a excellent screening assay with high discrimination power.

Example 11

Chemical Denaturation of a Nascent Polypeptide Determined by High Content Microscopy in a 96 Well Plate FIG. 24 shows the net fluorescent signal intensities obtained for imaged bead containing RNCS programmed with donor and donor plus acceptor—containing nascent polypeptides in a 96 well plate format. Nascent polypeptides contained the His-tag, CFP-NBD with the acceptor probe incorporated at residue Arg450 and truncated at residue 550 to allow the N-terminus subdomain to fold. For comparison, wild type NBD1 with and without the regulatory insertion were analyzed in parallel to compare domain stability. Added to wells were varying amounts of urea that ranged from 0 M to 6M. FRET values for each condition show a threshold concentration of urea in which FRET decreased indicating domain unfolding.

---

What is claimed is:

1. A method of detecting the folding of a protein domain, the method comprising:

performing cell free translation on a nucleic acid construct in the presence of a ribosome, the construct comprising a first polynucleotide that encodes the protein domain, a second polynucleotide that encodes a protein tag, and a third polynucleotide that encodes a FRET donor, the FRET donor having an emission wavelength, thereby generating a ribosome-nascent chain complex comprising the ribosome, the protein domain, the protein tag, and the FRET donor;

incorporating a FRET acceptor into the protein domain;

purifying the ribosome-nascent chain complex;

conjugating the ribosome-nascent chain complex to a solid substrate via the tag;

detecting a first fluorescence signal at the emission wavelength of the FRET donor, wherein a fluorescence signal that is lower than the fluorescence signal of a protein domain with a FRET donor but lacking a FRET acceptor indicates folding of the protein domain.

2. The method of claim 1 further comprising removing the ribosome from the ribosome-nascent chain complex by RNAse treatment after detecting the first fluorescence signal and further comprising detecting a second fluorescence signal after the ribosome is removed from the ribosome-nascent chain complex.

3. The method of claim 1 wherein the ribosome-nascent chain complex is purified by size exclusion chromatography.

4. The method of claim 1 further comprising incorporating a radioactive label into the protein domain and normalizing the fluorescence signal using the radioactive label.

5. The method of claim 4 wherein the FRET acceptor and/or the radioactive label is incorporated into the protein domain through the use of a labeled amino acid conjugated to a tRNA.

6. The method of claim 1 wherein the FRET donor is SEQ ID NO: 1 or a homolog thereof and wherein the FRET acceptor is 7-nitrobenz-2-oxa-1,3-diazolyl.

7. The method of claim 1 wherein the protein tag is SEQ ID NO: 11 and wherein the solid substrate comprises a nickel matrix.

8. The method of claim 7 wherein the ribosome-nascent chain complex is conjugated to the solid substrate at a density of at least 800 complexes per square micron.

9. The method of claim 1 wherein the protein domain is SEQ ID NO: 2 or a homolog thereof.

10. The method of claim 9 wherein the FRET acceptor is incorporated at residue T1 or residue V62 of SEQ ID NO: 2.

11. The method of claim 1 wherein the nucleic acid construct further comprises a fourth polynucleotide that encodes a flexible linker.

12. The method of claim 1 wherein the protein domain is a mutant protein domain, wherein the mutant protein domain is unable to properly fold, thereby resulting in a fluorescence signal that is greater than that of an unmutated protein domain.

13. The method of claim 12 wherein the mutant protein domain is SEQ ID NO: 7 or a homolog thereof.

14. The method of claim 12 further comprising contacting the ribosome-nascent chain complex comprising the mutant protein domain with a test compound, wherein a test compound that results in a fluorescent signal that is less than that of the mutant protein domain without the test compound identifies the test compound as promoting proper protein folding.

15. A kit that facilitates a method of detecting the folding of a protein domain, the kit comprising:
a first nucleic acid construct comprising a first polynucleotide that encodes a first protein domain, a second polynucleotide that encodes a protein tag, and a third polynucleotide that encodes a FRET donor;
a solid substrate;
a FRET acceptor that can be incorporated into the first protein domain; and
a reagent that promotes in vitro transcription, the reagent comprising a ribosome.

16. The kit of claim 15 wherein the FRET donor is SEQ ID NO: 1 or a homolog thereof and wherein the FRET acceptor is 7-nitrobenz-2-oxa-1,3-diazolyl.

17. The kit of claim 16 wherein the first protein domain is SEQ ID NO: 2 or a homolog thereof.

18. The kit of claim 15 wherein the protein tag is SEQ ID NO: 11 and wherein the solid substrate comprises a nickel matrix.

19. The kit of claim 15 wherein the reagent that promotes in vitro transcription is a rabbit reticulocyte lysate.

20. The kit of claim 15 further comprising a second nucleic acid construct comprising a second nucleic acid encoding a second protein domain, wherein the second protein domain is SEQ ID NO: 7 or a homolog thereof.

21. The kit of claim 15 further comprising a suppressor tRNA.

* * * * *